US012605142B2

(12) United States Patent
Hamada et al.

(10) Patent No.: US 12,605,142 B2
(45) Date of Patent: Apr. 21, 2026

(54) MATERIAL FOR ACOUSTIC MATCHING LAYER, ACOUSTIC MATCHING SHEET, ACOUSTIC WAVE PROBE, ULTRASOUND PROBE, ACOUSTIC WAVE MEASUREMENT APPARATUS, ULTRASOUND DIAGNOSTIC APPARATUS, AND METHOD FOR MANUFACTURING ACOUSTIC WAVE PROBE

(71) Applicant: FUJIFILM Corporation, Tokyo (JP)

(72) Inventors: Kazuhiro Hamada, Kanagawa (JP); Yoshihiro Nakai, Kanagawa (JP); Daisuke Hayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 891 days.

(21) Appl. No.: 17/939,429

(22) Filed: Sep. 7, 2022

(65) Prior Publication Data

US 2023/0037985 A1 Feb. 9, 2023

Related U.S. Application Data

(63) Continuation of application No. PCT/JP2021/009413, filed on Mar. 10, 2021.

(30) Foreign Application Priority Data

Mar. 18, 2020 (JP) ................................. 2020-048257

(51) Int. Cl.

| | |
|---|---|
| ***A61B 8/00*** | (2006.01) |
| ***B06B 1/06*** | (2006.01) |
| ***G01N 29/28*** | (2006.01) |

(52) U.S. Cl.

CPC .......... *A61B 8/4444* (2013.01); *A61B 8/4281* (2013.01); *A61B 8/4494* (2013.01); *B06B 1/067* (2013.01); *G01N 29/28* (2013.01)

(58) Field of Classification Search

CPC ... A61B 8/4272; A61B 8/4281; A61B 8/4444; A61B 8/4483; A61B 8/4494;

(Continued)

(56) References Cited

U.S. PATENT DOCUMENTS

2004/0113523 A1 6/2004 Hashimoto et al.
2008/0098816 A1 5/2008 Yamashita et al.

(Continued)

FOREIGN PATENT DOCUMENTS

CN 1522360 A 8/2004
CN 101172044 A 5/2008

(Continued)

OTHER PUBLICATIONS

Communication dated Jan. 22, 2025 in Chinese Application No. 202180018209.9.

(Continued)

*Primary Examiner* — Levi Gannon
(74) *Attorney, Agent, or Firm* — Sughrue Mion, PLLC

(57) ABSTRACT

A material for an acoustic matching layer contains the following components (A), (B), and (C):

(A) an epoxy resin;

(B) a curing agent; and (C) surface-treated tungsten carbide particles subjected to a surface treatment with a surface treatment agent including at least one of an aminosilane compound, a mercaptosilane compound, an isocyanatosilane compound, a thiocyanatosilane compound, an aluminum alkoxide compound, a zirconium alkoxide compound, or a titanium alkoxide compound.

20 Claims, 1 Drawing Sheet

(58) Field of Classification Search
CPC ...... B06B 1/067; G01N 29/28; G10K 11/002; G10K 11/02; G10K 11/18
See application file for complete search history.

(56) References Cited

U.S. PATENT DOCUMENTS

| | | | | |
|---|---|---|---|---|
| 2008/0303381 | A1 | 12/2008 | Yuuya et al. | |
| 2009/0062656 | A1* | 3/2009 | Hyuga | A61B 8/4488 600/459 |
| 2013/0133408 | A1 | 5/2013 | Lang | |
| 2014/0121525 | A1 | 5/2014 | Kusaka | |
| 2016/0155433 | A1* | 6/2016 | Siverson | B32B 38/0012 252/62 |
| 2019/0023831 | A1* | 1/2019 | Nagata | C08G 18/61 |
| 2019/0218394 | A1* | 7/2019 | Nagata | A61B 8/00 |
| 2020/0253582 | A1 | 8/2020 | Nakai et al. | |

FOREIGN PATENT DOCUMENTS

| | | | |
|---|---|---|---|
| CN | 103026183 | A | 4/2013 |
| CN | 103702617 | A | 4/2014 |
| JP | 2009-071393 | A | 4/2009 |
| JP | 2016-107076 | A | 6/2016 |
| JP | 2018-039992 | A | 3/2018 |
| WO | 2019/088148 | A1 | 5/2019 |

OTHER PUBLICATIONS

Extended European Search Report issued Jul. 17, 2023 in European Application No. 21770995.5.
International Search Report dated Apr. 20, 2021 in International Application No. PCT/JP2021/009413.
International Preliminary Report on Patentability dated Sep. 20, 2022 in International Application No. PCT/JP2021/009413.
Written Opinion of the International Searching Authority dated Apr. 20, 2021 in International Application No. PCT/JP2021/009413.
Notice of Reasons for Refusal dated Jan. 17, 2023 from Japanese Patent Office in application No. 2022-508247.

* cited by examiner

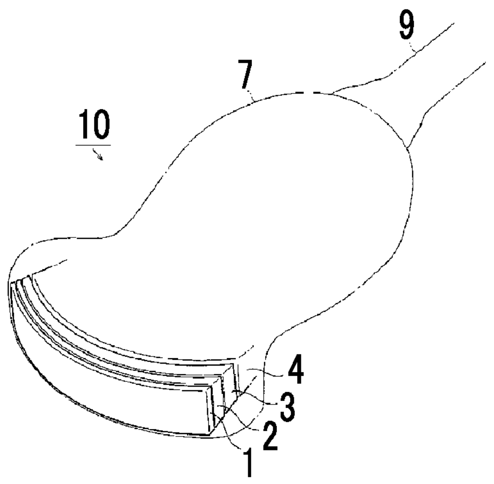
9
7
10
4
3
2
1

MATERIAL FOR ACOUSTIC MATCHING LAYER, ACOUSTIC MATCHING SHEET, ACOUSTIC WAVE PROBE, ULTRASOUND PROBE, ACOUSTIC WAVE MEASUREMENT APPARATUS, ULTRASOUND DIAGNOSTIC APPARATUS, AND METHOD FOR MANUFACTURING ACOUSTIC WAVE PROBE

CROSS-REFERENCE TO RELATED APPLICATIONS

This application is a Continuation of PCT International Application No. PCT/JP2021/009413 filed on Mar. 10, 2021, which claims priority under 35 U.S.C § 119(a) to Japanese Patent Application No. 2020-048257 filed on Mar. 18, 2020. Each of the above application(s) is hereby expressly incorporated by reference, in its entirety, into the present application.

BACKGROUND OF THE INVENTION

1. Field of the Invention

The present invention relates to a material for an acoustic matching layer, an acoustic matching sheet, an acoustic wave probe, an ultrasound probe, an acoustic wave measurement apparatus, an ultrasound diagnostic apparatus, and a method for manufacturing an acoustic wave probe.

2. Description of the Related Art

In an acoustic wave measurement apparatus, an acoustic wave probe is used which irradiates a test object such as a living body with an acoustic wave, receives a reflected wave (echo) therefrom, and outputs a signal. The reflected wave received by this acoustic wave probe is converted into an electric signal which is displayed as an image. Therefore, by using the acoustic wave probe, it is possible to visualize and observe an inside of the test object.

An ultrasonic wave, a photoacoustic wave, or the like is appropriately selected as the acoustic wave according to the test object or measurement conditions.

For example, an ultrasound diagnostic apparatus, which is a kind of the acoustic wave measurement apparatus, transmits an ultrasonic wave to the inside of the test object, receives the ultrasonic wave reflected by tissues inside the test object, and displays the received ultrasonic wave as an image.

In addition, a photoacoustic wave measurement apparatus, which is a kind of the acoustic wave measurement apparatus, receives an acoustic wave radiated from the inside of the test object due to a photoacoustic effect, and displays the received acoustic wave as an image. The photoacoustic effect is a phenomenon in which an acoustic wave (typically, an ultrasonic wave) is generated through thermal expansion after the test object absorbs an electromagnetic wave to generate heat in a case where the test object is irradiated with an electromagnetic wave pulse of visible light, near infrared light, microwave, or the like.

Since the acoustic wave measurement apparatus transmits and receives an acoustic wave to and from the test object, the acoustic wave probe is required to match an acoustic impedance with the test object (typically, a human body). In order to satisfy this requirement, the acoustic wave probe is provided with an acoustic matching layer. This will be described by taking, as an example, a probe for an ultrasound diagnostic apparatus (also referred to as an ultrasound probe), which is a kind of the acoustic wave probe.

The ultrasound probe includes a piezoelectric element that transmits and receives an ultrasonic wave and an acoustic lens which comes into contact with a living body, in which an acoustic matching layer is disposed between the piezoelectric element and the acoustic lens. An ultrasonic wave oscillated from the piezoelectric element is incident on the living body after being transmitted through the acoustic matching layer, further being transmitted through the acoustic lens. There is usually a difference in acoustic impedance (density × acoustic velocity) between the acoustic lens and the living body. In a case where this difference is large, the ultrasonic wave is easily reflected on a surface of the living body, and an incident efficiency of the ultrasonic wave into the living body is lowered. Therefore, the acoustic lens is required to have an acoustic impedance characteristic close to that of the living body.

On the other hand, the difference in acoustic impedance between the piezoelectric element and the living body is generally large. Accordingly, the difference in acoustic impedance between the piezoelectric element and the acoustic lens is also usually large. Therefore, in a case of a laminated structure of the piezoelectric element and the acoustic lens, the ultrasonic wave emitted from the piezoelectric element is reflected on a surface of the acoustic lens, and the incident efficiency of the ultrasonic wave into the living body is lowered. In order to suppress this reflection of the ultrasonic wave, the above-described acoustic matching layer is provided between the piezoelectric element and the acoustic lens. The acoustic impedance of the acoustic matching layer takes a value between the acoustic impedance of the living body or the acoustic lens and the acoustic impedance of the piezoelectric element, which leads to improved propagation efficiency of an ultrasonic wave from the piezoelectric element to the living body. In addition, in recent years, the development of an acoustic matching layer with more efficient propagation of an ultrasonic wave has been underway by providing a gradient in acoustic impedance from the piezoelectric element side to the acoustic lens side, through a configuration of an acoustic matching layer having a multi-layer structure in which a plurality of acoustic matching sheets (sheet-like acoustic matching layer materials) are laminated.

The acoustic impedance of the acoustic matching layer can be adjusted by formulating a filler such as metal particles in a material for forming the acoustic matching layer. For example, WO2019/088148A discloses a resin composition for an acoustic matching layer, which includes a binder including a resin such as an epoxy resin and surface-treated metal particles.

SUMMARY OF THE INVENTION

In the acoustic matching layer having a multi-layer structure, the above-described gradient of the acoustic impedance is designed such that the closer it is to the piezoelectric element, the larger the acoustic impedance of the acoustic matching sheet, and the closer it is to the acoustic lens, the smaller the acoustic impedance of the acoustic matching sheet. That is, an acoustic matching sheet having acoustic impedance close to the acoustic impedance of the piezoelectric element (usually, approximately 25 Mrayl) is required on the piezoelectric element side; and an acoustic matching sheet having acoustic impedance close to the acoustic impedance of the living body (1.4 to 1.7 Mrayl in the human body) is required on the acoustic lens side.

The acoustic impedance of the acoustic matching sheet is determined by multiplying a density and an acoustic velocity of a sheet constituent material. Therefore, in a case of trying to increase the acoustic impedance of the acoustic matching sheet used on the piezoelectric element side, it is conceivable to use a material having a high density and a high acoustic velocity. However, in a case where a filler such as a metal having a large specific gravity is contained in the acoustic matching sheet in order to increase the acoustic impedance, it has been found that, while the density of the sheet can be improved, the acoustic velocity of the sheet decreases. Therefore, in a case where a filler such as a metal having a large specific gravity is used for the acoustic matching sheet, in order to use this sheet on the piezoelectric element side, it is necessary to suppress the above-described decrease in acoustic velocity. However, WO2019/088148A does not disclose this point.

An object of the present invention is to provide a material for an acoustic matching layer in which, while using tungsten carbide particles having a large specific gravity as a metal filler, it is possible to effectively increase an acoustic impedance of an acoustic matching sheet obtained by suppressing a decrease in acoustic velocity due to the formulation of the tungsten carbide particles, and it is also possible to suppress variations in acoustic characteristics in this acoustic matching sheet.

Another object of the present invention is to provide an acoustic matching sheet in which, while using tungsten carbide particles as a metal filler, a decrease in acoustic velocity due to the formulation of the tungsten carbide particles is suppressed so that an acoustic impedance is effectively increased, and variations of acoustic characteristics in the sheet are also suppressed.

Another object of the present invention is to provide an acoustic wave probe and an ultrasound probe using the acoustic matching sheet, and an acoustic wave measurement apparatus and an ultrasound diagnostic apparatus using these.

Another object of the present invention is to provide a method for manufacturing an acoustic wave probe using the material for an acoustic matching layer.

As a result of intensive studies in view of the above-described problems, the present inventors have found that, in a case where an epoxy resin and a curing agent are subjected to a curing reaction in the presence of tungsten carbide particles treated with a specific surface treatment agent to produce an acoustic matching sheet, it is possible to suppress the decrease in acoustic velocity, which normally occurs due to the containing of the tungsten carbide particles, and that this acoustic matching sheet has little variations in acoustic characteristics. The present invention has been completed based on these findings.

The foregoing objects of the present invention have been achieved by the following means.

<1>

A material for an acoustic matching layer, comprising the following components (A), (B), and (C):

(A) an epoxy resin;

(B) a curing agent; and (C) surface-treated tungsten carbide particles subjected to a surface treatment with a surface treatment agent including at least one of an aminosilane compound, a mercaptosilane compound, an isocyanatosilane compound, a thiocyanatosilane compound, an aluminum alkoxide compound, a zirconium alkoxide compound, or a titanium alkoxide compound.

<2>

The material for an acoustic matching layer according to <1>, in which the component (B) includes at least one of a primary amine or a secondary amine.

<3>

The material for an acoustic matching layer according to <1> or <2>, in which the surface treatment agent includes at least one of an aminosilane compound, an aluminum alkoxide compound, a zirconium alkoxide compound, or a titanium alkoxide compound.

<4>

The material for an acoustic matching layer according to any one of <1> to <3>, in which the surface treatment agent includes at least one of an aluminum alkoxide compound, a zirconium alkoxide compound, or a titanium alkoxide compound.

<5>

The material for an acoustic matching layer according to any one of <1> to <4>, in which the surface treatment agent includes at least one of a zirconium alkoxide compound or a titanium alkoxide compound.

<6>

The material for an acoustic matching layer according to any one of <1> to <5>, in which the aluminum alkoxide compound includes at least one of an acetonato structure or an acetato structure.

<7>

The material for an acoustic matching layer according to any one of <1> to <6>, in which the aluminum alkoxide compound includes at least one compound represented by General Formula (1), $R^{1a}_{m1}$-Al—$(OR^{2a})_{3-m1}$ General Formula (1):

where $R^{1a}$ represents a hydrogen atom, an alkyl group, a cycloalkyl group, an acyl group, an aryl group, or an unsaturated aliphatic group, $R^{2a}$ represents a hydrogen atom, an alkyl group, a cycloalkyl group, an acyl group, an alkenyl group, an aryl group, a phosphonate group, or —$SO_2R^{S1}$, $R^{S1}$ represents a substituent, and m1 is an integer of 0 to 2.

<8>

The material for an acoustic matching layer according to any one of <1> to <7>, in which the zirconium alkoxide compound includes at least one of an acetonato structure or an acetato structure.

<9>

The material for an acoustic matching layer according to any one of <1> to <8>, in which the zirconium alkoxide compound includes at least one compound represented by General Formula (2), $R^{1b}_{m2}$-Zr—$(OR^{2b})_{4-m2}$ General Formula (2):

where $R^{1b}$ represents a hydrogen atom, an alkyl group, a cycloalkyl group, an acyl group, an aryl group, or an unsaturated aliphatic group, $R^{2b}$ represents a hydrogen atom, an alkyl group, a cycloalkyl group, an acyl group, an alkenyl group, an aryl group, a phosphonate group, or —$SO_2R^{S2}$, $R^{S2}$ represents a substituent, and m2 is an integer of 0 to 3.

<10>

The material for an acoustic matching layer according to any one of <1> to <9>, in which the titanium alkoxide compound includes at least one atom of N, P, or S.

<11>

The material for an acoustic matching layer according to any one of <1> to <10>, in which the titanium alkoxide compound includes at least one compound represented by General Formula (3), $$R^{1c}_{m3}\text{-Ti—}(OR^{2c})_{4\text{-}m3} \qquad \text{General Formula (3):}$$

where $R^{1c}$ represents a hydrogen atom, an alkyl group, a cycloalkyl group, an acyl group, an aryl group, or an unsaturated aliphatic group, $R^{2c}$ represents a hydrogen atom, an alkyl group, a cycloalkyl group, an acyl group, an alkenyl group, an aryl group, a phosphonate group, or $—SO_2R^{S3}$, $R^{S3}$ represents a substituent, and m3 is an integer of 0 to 3.

<12>

The material for an acoustic matching layer according to any one of <1> to <11>, in which a content of the surface treatment agent in the component (C) is 1 to 50 parts by mass with respect to 100 parts by mass of the surface-treated tungsten carbide particles.

<13>

The material for an acoustic matching layer according to any one of <1> to <12>, in which an average primary particle diameter of the surface-treated tungsten carbide particles constituting the component (C) is 1 to 10 μm.

<14>

An acoustic matching sheet obtained by curing the material for an acoustic matching layer according to any one of <1> to <13>.

<15>

An acoustic wave probe comprising:

the acoustic matching sheet according to <14>.

<16>

An ultrasound probe comprising:

the acoustic matching sheet according to <14>.

<17>

An acoustic wave measurement apparatus comprising:

the acoustic wave probe according to <15>.

<18>

An ultrasound diagnostic apparatus comprising:

the ultrasound probe according to <16>.

<19>

A method for manufacturing an acoustic wave probe, comprising:

forming an acoustic matching layer using the material for an acoustic matching layer according to any one of <1> to <13>.

In the description of the present specification, a "metal alkoxide compound (specifically, for example, a titanium alkoxide compound, an aluminum alkoxide compound, or a zirconium alkoxide compound which will be described later)" means a compound having a structure in which at least one alkoxy group is bonded to a metal atom. The alkoxy group may have a substituent. The substituent may be monovalent or divalent (for example, an alkylidene group). In addition, two alkoxy groups bonded to one metal atom may be bonded to each other to form a ring.

In the description of the present specification, unless otherwise specified, in a case where a plurality of groups having the same reference numerals are present in the general formula representing a compound, the groups may be the same or different from each other. In addition, the group specified by each group (for example, an alkyl group) may further have a substituent.

In addition, the expression "to" in the present specification is used to mean that numerical values described before and after "to" are included as a lower limit value and an upper limit value, respectively.

With the material for an acoustic matching layer according to the aspect of the present invention, while using tungsten carbide particles having a large specific gravity as a metal filler, it is possible to effectively increase an acoustic impedance of an acoustic matching sheet obtained by suppressing a decrease in acoustic velocity due to the formulation of the tungsten carbide particles, and it is also possible to reduce variations in acoustic characteristics in this acoustic matching sheet.

In addition, with the acoustic matching sheet according to the aspect of the present invention, while using tungsten carbide particles as a metal filler, a decrease in acoustic velocity due to the formulation of the tungsten carbide particles is suppressed so that an acoustic impedance is effectively increased, and variations of acoustic characteristics in the sheet are also reduced.

In addition, the acoustic wave probe, the ultrasound probe, the acoustic wave measurement apparatus, and the ultrasound diagnostic apparatus according to the aspects of the present invention include the acoustic matching sheet with the above-described excellent characteristics.

In addition, with the method for manufacturing an acoustic wave probe according to the aspect of the present invention, an acoustic wave probe using the above-described material for an acoustic matching layer can be obtained.

BRIEF DESCRIPTION OF THE DRAWINGS

FIG. 1 is a perspective view of an example of a convex type ultrasound probe which is an aspect of an acoustic wave probe.

DESCRIPTION OF THE PREFERRED EMBODIMENTS

<<Material for Acoustic Matching Layer>>

A material for an acoustic matching layer (hereinafter, also simply referred to as a "material") according to an embodiment of the present invention contains the following components (A), (B), and (C).

(A) an epoxy resin (B) a curing agent (C) surface-treated tungsten carbide particles subjected to a surface treatment with a surface treatment agent of at least one kind of an aminosilane compound, a mercaptosilane compound, an isocyanatosilane compound, a thiocyanatosilane compound, an aluminum alkoxide compound, a zirconium alkoxide compound, or a titanium alkoxide compound The material according to the embodiment of the present invention includes a form of a composition obtained by mixing the above-described components (A) to (C). In a case where the material according to the embodiment of the present invention is in a form of a composition for an acoustic matching layer (hereinafter, also referred to as a "composition" according to the embodiment of the present invention), that is, a case where the above-described components (A) to (C) are mixed and contained in a container, in order to keep each component stable, it is preferable to store the composition at −10° C. or lower so that the above-described components (A) to (C) do not cause a reaction or are sufficiently suppressed.

The material according to the embodiment of the present invention includes a form of a set for an acoustic matching layer (hereinafter, also referred to as a "set" according to the embodiment of the present invention) contained in a container in a state in which the above-described components (A) to (C) are further separated. Examples of the form of this set include the following aspects (i) to (iv).

(i) aspect in which the above-described components (A) and (B) and the above-described component (C) are separately contained and mixed during use
(ii) aspect in which the above-described components (A) and (C) and the above-described component (B) are separately contained and mixed during use
(iii) aspect in which the above-described component (A) and the above-described components (B) and (C) are separately contained and mixed during use
(iv) aspect in which the above-described components (A) to (C) are separately contained and mixed during use In the above-described aspects (i) to (iv), in order to keep each component stable, it is preferable to store the set according to the embodiment of the present invention at −10° C. or lower.

The material according to the embodiment of the present invention may be stored in a light-shielded manner, if necessary.

In a case where an acoustic matching sheet contains a filler with a large specific gravity, an acoustic velocity of the sheet decreases. It is presumed that, due to the inertia in a case where an acoustic wave (mainly, a longitudinal wave) penetrates into the acoustic matching sheet, the phase is delayed at a filler interface and the acoustic velocity is lowered. However, in the acoustic matching sheet according to the present invention, which is obtained by curing the material according to the embodiment of the present invention having the above-described configuration, a decrease in acoustic velocity (acoustic velocity=(elastic modulus of sheet/density of sheet)$^{1/2}$) is suppressed, and variations in acoustic characteristics are reduced. The reasons for these effects are not clear yet, but it is presumed as follows. In the acoustic matching sheet according to the present invention, since the component (C) is surface-treated with a specific surface treatment agent, it is considered that a structure which contributes to improving the elastic modulus of the sheet is formed at an interface between the component (C) and a matrix resin, and while suppressing an aggregation of the component (C), the elastic modulus is increased by a slight aggregation of the small amount of the component (C).

<(A) Epoxy Resin>

As the epoxy resin used in the present invention, an ordinary epoxy resin can be used, and for example, a bisphenol A type epoxy resin, a bisphenol F type epoxy resin, or a phenol novolac type epoxy resin is preferable.

The bisphenol A type epoxy resin used in the present invention is not particularly limited, and any bisphenol A type epoxy resin commonly used as a main agent of an epoxy-based adhesive can be widely used. Preferred specific examples thereof include bisphenol A diglycidyl ethers (jER825, jER828, and jER834 (all trade names), manufactured by Mitsubishi Chemical Corporation) and bisphenol A propoxylate diglycidyl ethers (manufactured by Sigma-Aldrich Co. LLC).

The bisphenol F type epoxy resin used in the present invention is not particularly limited, and any bisphenol F type epoxy resin commonly used as a main agent of an epoxy-based adhesive can be widely used. Preferred specific examples thereof include bisphenol F diglycidyl ether (trade name: EPICLON 830, manufactured by DIC Corporation) and 4,4'-methylenebis(N,N-diglycidylaniline).

The phenol novolac type epoxy resin used in the present invention is not particularly limited, and any phenol novolac type epoxy resin commonly used as a main agent of an epoxy-based adhesive can be widely used. Such a phenol novolac type epoxy resin is commercially available, for example, by the product number 406775 from Sigma-Aldrich Co. LLC.

<(B) Curing Agent>

As the curing agent, one (preferably, an organic compound) known as a curing agent for an epoxy resin can be used without particular limitation. Examples thereof include an aliphatic amine, an aromatic amine, a dicyandiamide, a dihydrazide compound, an acid anhydride, and a phenol compound.

From the viewpoint of increasing a crosslink density and further reducing variations in acoustic characteristics of the obtained material, it is preferable to use at least one kind of a primary amine (compound having an unsubstituted amino group) or a secondary amine (compound having a monosubstituted amino group), and it is more preferable to use a primary amine. A compound having both an unsubstituted amino group and a monosubstituted amino group is classified as the secondary amine. Specific examples of the compound having at least one kind of an unsubstituted amino group or a monosubstituted amino group include isophorone diamine, menthanediamine, m-phenylenediamine, polyetheramine, polyamidoamine, triethylenetetramine, and piperidine.

<(C) Surface-Treated Tungsten Carbide Particles>

The component (C) is surface-treated tungsten carbide particles subjected to a surface treatment with a surface treatment agent including at least one kind of an aminosilane compound, a mercaptosilane compound, an isocyanatosilane compound, a thiocyanatosilane compound, an aluminum alkoxide compound, a zirconium alkoxide compound, or a titanium alkoxide compound. The component (C) is a component different from the component (B).

An average primary particle diameter of the tungsten carbide particles constituting the surface-treated tungsten carbide particles used in the present invention is not particularly limited, but from the viewpoint of suppressing the decrease in acoustic velocity of the acoustic matching sheet and viewpoint of reducing the variations in acoustic characteristics of the acoustic matching sheet, it is preferably 1 to 30 μm, more preferably 1 to 20 μm, and still more preferably 1 to 10 μm.

An average primary particle diameter of the component (C) is preferably 1 to 30 μm, more preferably 1 to 20 μm, and still more preferably 1 to 10 μm.

The average primary particle diameter can be obtained by averaging particle diameters which are measured by a transmission electron microscope (TEM). That is, the shortest diameter and longest diameter of one tungsten carbide particle in an electron micrograph captured by TEM are measured, and the arithmetic mean value thereof is obtained as a particle diameter of one tungsten carbide particle. In the present invention, particle diameters of 300 randomly selected tungsten carbide particles are averaged and determined as the average primary particle diameter.

Commercially available tungsten carbide particles can be used, and examples thereof include WC (trade name) manufactured by A.L.M.T. Corp.

From the viewpoint of suppressing the decrease in acoustic velocity of the acoustic matching sheet and viewpoint of reducing the variations in acoustic characteristics of the acoustic matching sheet, the surface treatment agent used in the present invention preferably includes at least one kind of an aminosilane compound, an aluminum alkoxide compound, a zirconium alkoxide compound, or a titanium alkoxide compound, more preferably includes at least one kind of an aluminum alkoxide compound, a zirconium alkoxide compound, or a titanium alkoxide compound, and still more preferably includes at least one kind of a zirconium alkoxide compound or a titanium alkoxide compound.

Hereinafter, the surface treatment agent used in the present invention will be specifically described.

(Aminosilane Compound)

The aminosilane compound (silane compound having an amino group) is preferably a silane coupling agent having an amino group. However, it is preferable that the above-described aminosilane compound does not have a Si—N—Si structure. In a "Si—N—Si structure", each silicon atom has three bonding sites and the nitrogen atom has one bonding site.

The aminosilane compound preferably includes at least one compound represented by General Formula (A).

General Formula (A)

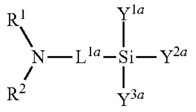

In the formula, $R^1$ and $R^2$ represent a hydrogen atom or a substituent. $L^{1a}$ represents a single bond, an alkylene group, an alkenylene group, an alkynylene group, an arylene group, —O—, —S—, —$NR^a$—, an ester bond, a thioester bond, an amide bond, a thioamide bond or a sulfonyl group, or a divalent group consisting of a combination of two or more of these groups or bonds. $R^a$ represents a hydrogen atom or a substituent. $Y^{1a}$ represents a hydroxy group or an alkoxy group. $Y^{2a}$ and $Y^{3a}$ represent a hydroxy group, an alkoxy group, an alkyl group, or a ketoxime group.

Examples of the substituent that can be used as $R^1$ and $R^2$ include an alkyl group (preferably having 1 to 12 carbon atoms and more preferably 1 to 8 carbon atoms), an alkenyl group (preferably having 2 to 12 carbon atoms and more preferably 2 to 8 carbon atoms), an alkynyl group (preferably having 2 to 12 carbon atoms and more preferably 2 to 8 carbon atoms), and an aryl group (preferably having 6 to 20 carbon atoms and more preferably 6 to 10 carbon atoms). These substituents may further have a substituent, and examples of such a substituent include the above-described substituents mentioned as a substituent that can be used as $R^1$ and $R^2$ and an amino group.

In addition, $R^1$ and $R^2$ may be combined to represent an alkylidene group (preferably having 2 to 12 carbon atoms and more preferably 2 to 8 carbon atoms).

$L^{1a}$ preferably represents an alkylene group, an alkenylene group, an arylene group, —O—, or —$NR^a$—, more preferably an alkylene group, an arylene group, or —$NR^a$—, and still more preferably an alkylene group.

$Y^{1a}$ preferably represents an alkoxy group.

$Y^{2a}$ and $Y^{3a}$ preferably represent a hydroxy group, an alkoxy group, or an alkyl group, and more preferably an alkoxy group or an alkyl group.

The alkylene group that can be used as $L^{1a}$ may be linear, branched, or cyclic. The number of carbon atoms in the alkylene group is preferably 1 to 30, more preferably 1 to 25, still more preferably 1 to 20, and even still more preferably 1 to 15. Specific examples of the alkylene group include methylene, ethylene, propylene, tert-butylene, pentylene, cyclohexylene, heptylene, octylene, nonylene, decylene, and undecylene.

The alkenylene group that can be used as $L^{1a}$ may be linear or branched. The number of carbon atoms in the alkenylene group is preferably 2 to 20, more preferably 2 to 15, still more preferably 2 to 10, and even still more preferably 2 to 6. Specific examples of the alkenylene group include ethenylene and propenylene.

The alkynylene group that can be used as $L^{1a}$ may be linear or branched. The number of carbon atoms in the alkynylene group is preferably 2 to 20, more preferably 2 to 15, still more preferably 2 to 10, and even still more preferably 2 to 6. Specific examples of the alkynylene group include ethynylene and propynylene.

The number of carbon atoms in the arylene group that can be used as $L^{1a}$ is preferably 6 to 20, more preferably 6 to 15, still more preferably 6 to 12, and even still more preferably 6 to 10. Specific examples of the arylene group include phenylene and naphthylene.

Examples of the substituent that can be used as $R^a$ of —$NR^a$— include an alkyl group (preferably having 1 to 12 carbon atoms and more preferably 1 to 8 carbon atoms), an alkenyl group (preferably having 2 to 12 carbon atoms and more preferably 2 to 8 carbon atoms), an alkynyl group (preferably having 2 to 12 carbon atoms and more preferably 2 to 8 carbon atoms), an aryl group (preferably having 6 to 20 carbon atoms and more preferably 6 to 10 carbon atoms), and a heterocyclic group. A heterocyclic ring constituting the heterocyclic group that can be used as $R^a$ may be a saturated or unsaturated aliphatic heterocyclic ring or aromatic heterocyclic ring, and may be a monocyclic ring or a fused ring. In addition, the heterocyclic ring may also be a bridged ring. Examples of the heteroatom contained in the heterocyclic ring include an oxygen atom, a nitrogen atom, and a sulfur atom. The number of heteroatoms contained in one heterocyclic ring is not particularly limited, but is preferably 1 to 3 and more preferably 1 or 2. The number of carbon atoms in the heterocyclic ring is preferably 2 to 10 and more preferably 4 or 5. The heterocyclic ring is preferably a 3- to 7-membered ring, more preferably a 3- to 6-membered ring, and still more preferably a 3- to 5-membered ring. Specific examples of the heterocyclic ring include an epoxy ring, a 3,4-epoxycyclohexane ring, a furan ring, and a thiophene ring.

Examples of —$NR^a$— include —NH—.

The number of groups or bonds to be combined that constitute a divalent group consisting of a combination of two or more of the above-described groups or the above-described bonds that can be used as $L^{1a}$ (hereinafter, also referred to as a "group consisting of a combination that can be used as $L^{1a}$") is preferably 2 to 8, more preferably 2 to 6, and still more preferably 2 to 4.

In addition, the molecular weight of the group consisting of a combination that can be used as $L^{1a}$ is preferably 20 to 1,000, more preferably 30 to 500, and still more preferably 40 to 200.

Examples of the group consisting of a combination that can be used as $L^{1a}$ include a urea bond, a thiourea bond, a carbamate group, a sulfonamide bond, arylene-alkylene, —O-alkylene, amide bond-alkylene, —S-alkylene, alkylene-O-amide bond-alkylene, alkylene-amide bond-alkylene, alkenylene-amide bond-alkylene, alkylene-ester bond-alkylene, arylene-ester bond-alkylene, -(alkylene-O)—, alkylene-O-(alkylene-O)-alkylene (in which "(alkylene-O)" is a repeating unit), arylene-sulfonyl-O-alkylene, and ester bond-alkylene.

The alkyl group constituting the alkoxy group that can be used as $Y^{1a}$ to $Y^{3a}$ may be linear, branched, or cyclic, and may have a combination of these forms. In the present invention, the alkyl group is preferably a linear alkyl group. The number of carbon atoms in the alkyl group constituting the alkoxy group is preferably 1 to 15, more preferably 1 to 10, still more preferably 1 to 5, and even still more preferably 1 or 2. Specific examples of the alkyl group constituting the alkoxy group include methyl, ethyl, propyl, t-butyl, pentyl, and cyclohexyl.

Examples of the alkyl group that can be used as $Y^{2a}$ and $Y^{3a}$ include an alkyl group that constitutes the alkoxy group that can be used as $Y^{1a}$ to $Y^{3a}$, and a preferred form thereof is also the same as the preferred form of the alkyl group that constitutes the alkoxy group that can be used as $Y^{1a}$ to $Y^{3a}$.

The ketoxime group that can be used as $Y^{2a}$ and $Y^{3a}$ is a substituent having the following structure.

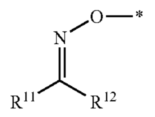

In the above-described structure, $R^{11}$ and $R^{12}$ represent a substituent, and * represents a bonding portion to a silicon atom.

Examples of the substituent that can be used by $R^{11}$ and $R^{12}$ include the substituents in $R^a$, and a preferred form thereof is also the same as the preferred form of the substituent that can be used as $R^a$.

Examples of the ketoxime group include a dimethyl ketoxime group, a methyl ethyl ketoxime group, and a diethyl ketoxime group.

Hereinafter, specific examples of the aminosilane compound used in the present invention will be given, but the present invention is not limited thereto.

3-Aminopropyltrimethoxysilane
3-Aminopropyldimethylmethoxysilane
3-Aminopropylmethyldimethoxysilane
3-Aminopropylmethyldiethoxysilane
3-Aminopropyltriethoxysilane
N-(2-aminoethyl)-3-aminopropylmethyldimethoxysilane
N-(2-aminoethyl)-3-aminopropylmethyldiethoxysilane
N-(2-aminoethyl)-3-aminopropyltrimethoxysilane
N-(2-aminoethyl)-3-aminopropyltriethoxysilane
3-Methyldimethoxysilyl-N-(1,3-dimethyl-butylidene)propylamine
3-Methyldiethoxysilyl-N-(1,3-dimethyl-butylidene)propylamine)
3-Trimethoxysilyl-N-(1,3-dimethyl-butylidene)propylamine
3-Triethoxysilyl-N-(1,3-dimethyl-butylidene)propylamine
N-phenyl-3-aminopropylmethyldimethoxysilane
N-phenyl-3-aminopropylmethyldiethoxysilane
N-Phenyl-3-aminopropyltrimethoxysilane
N-Phenyl-3-aminopropyltriethoxysilane
N-(vinylbenzyl)-2-aminoethyl-3-aminopropyltrimethoxysilane (Mercaptosilane Compound)

The mercaptosilane compound (silane compound having a mercapto group (sulfanyl group)) is preferably a silane coupling agent having a mercapto group. The tungsten carbide particles surface-treated with a mercaptosilane compound preferably have a mercapto group derived from the mercaptosilane compound.

The mercaptosilane compound preferably includes at least one compound represented by General Formula (B).

General Formula (B)

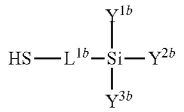

$L^{1b}$, $Y^{1b}$, $Y^{2b}$, and $Y^{3b}$ have the same definition as $L^{1a}$, $Y^{1a}$, $Y^{2a}$ and $Y^{3a}$ of General Formula (A), respectively, and preferred ranges thereof are also the same as in General Formula (A).

Hereinafter, specific examples of the mercaptosilane compound used in the present invention will be given, but the present invention is not limited thereto.

3-Mercaptopropyltrimethoxysilane
3-Mercaptopropyltriethoxysilane
3-Mercaptopropylmethyldimethoxysilane
Mercaptomethylmethyldiethoxysilane
(Mercaptomethyl)methyldimethoxysilane
(Mercaptomethyl)dimethylethoxysilane
11-Mercaptoundecyltrimethoxysilane (Isocyanatosilane Compound)

The isocyanatosilane compound (preferably a silane compound having an isocyanato group) is preferably a silane coupling agent having an isocyanato group. The tungsten carbide particles surface-treated with an isocyanatosilane compound preferably have an isocyanato group derived from the isocyanatosilane compound.

The isocyanatosilane compound preferably includes at least one compound represented by General Formula (C).

General Formula (C)

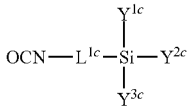

$L^{1c}$, $Y^{1c}$, $Y^{2c}$, and $Y^{3c}$ have the same definition as $L^{1a}$, $Y^{1a}$, $Y^{2a}$, and $Y^{3a}$ of General Formula (A), respectively, and preferred ranges thereof are also the same as in General Formula (A).

In addition, in the present invention, it is also preferable to use, as the isocyanatosilane compound, a condensate of the above-described compound represented by General Formula (C) and a compound in which the isocyanato group of General Formula (C) is protected by a substituent. The substituent can be introduced by, for example, an alcohol compound, a phenol compound, an aromatic amine, a lactam, or an oxime. Examples of such an alcohol compound include an alkyl alcohol (preferably having 1 to 12 carbon atoms and more preferably 1 to 8 carbon atoms). In addition, examples of the phenol compound include a phenol and a cresol. In addition, examples of the lactam include an ε-caprolactam.

The "compound in which the isocyanato group of General Formula (C) is protected by a substituent" is a compound in which —NCO of General Formula (C) is substituted with —NHC(=O)OR$^4$. R$^4$ represents a substituent, examples of which include an alkyl group (preferably having 1 to 12 carbon atoms and more preferably 1 to 8 carbon atoms).

Hereinafter, specific examples of the isocyanatosilane compound used in the present invention will be given, but the present invention is not limited thereto.

3-Isocyanatopropyltrimethoxysilane
3-Isocyanatopropyltriethoxysilane
Isocyanatomethyltrimethoxysilane
(the following are condensed isocyanatosilane compounds and isocyanatosilane compounds protected by a substituent)
Tris(3-trimethoxysilylpropyl)isocyanurate
(3-Triethoxysilylpropyl)-t-butylcarbamate
Tri(ethoxysilyl)propylethylcarbamate (Thiocyanatosilane Compound)

The thiocyanatosilane compound (silane compound having a thiocyanato group) is preferably a silane coupling agent having a thiocyanato group. The tungsten carbide particles surface-treated with a thiocyanatosilane compound preferably have a thiocyanato group derived from the thiocyanatosilane compound.

The thiocyanatosilane compound preferably includes at least one compound represented by General Formula (D).

General Formula (D)

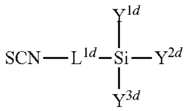

L$^{1d}$, Y$^{1d}$, Y$^{2d}$, and Y$^{3d}$ have the same definition as L$^{1a}$, Y$^{1a}$, Y$^{2a}$, and Y$^{3a}$ of General Formula (A), respectively, and preferred ranges thereof are also the same as in General Formula (A).

Hereinafter, specific examples of the thiocyanatosilane compound used in the present invention will be given, but the present invention is not limited thereto.

3-Thiocyanatopropyltrimethoxysilane
3-Thiocyantopropyltriethoxysilane
Thiocyanatomethyltrimethoxysilane (Aluminum Alkoxide Compound)

It is preferable that the aluminum alkoxide compound includes at least one kind of an acetonato structure or an acetato structure.

The aluminum alkoxide compound preferably includes at least one compound represented by General Formula (1).

$$R^{1a}{}_{m1}\text{-Al—}(OR^{2a})_{3-m1} \qquad \text{General Formula (1):}$$

R$^{1a}$ represents a hydrogen atom, an alkyl group, a cycloalkyl group, an acyl group, an aryl group, or an unsaturated aliphatic group.

The alkyl group that can be used as R$^{1a}$ includes a linear alkyl group, a branched alkyl group, and an aralkyl group. The number of carbon atoms in the alkyl group is preferably 1 to 20, more preferably 1 to 15, still more preferably 1 to 10, and particularly preferably 1 to 8, and in a case of an aralkyl group, the number of carbon atoms in the alkyl group is preferably 7 to 30. Preferred specific examples of the alkyl group include methyl, ethyl, propyl, isopropyl, butyl, sec-butyl, isobutyl, tert-butyl, pentyl, hexyl, heptyl, octyl, decyl, tridecyl, octadecyl, benzyl, and phenethyl.

It is also preferable that the alkyl group that can be used as R$^{1a}$ has an oxirane ring. The number of ring members in the cycloalkyl group (cycloalkyl group having a structure in which an oxirane ring is condensed) in the epoxycycloalkyl group that can be used as R$^{1a}$ is preferably 4 to 8, more preferably 5 or 6, and still more preferably 6 (that is, an epoxycyclohexyl group).

In addition, the alkyl group that can be used as R$^{1a}$ preferably has a group selected from an amino group, an isocyanato group, a mercapto group, an ethylenic unsaturated group, and an acid anhydride group.

The cycloalkyl group that can be used as R$^{1a}$ preferably has 3 to 20 carbon atoms, more preferably 3 to 15 carbon atoms, still more preferably 3 to 10 carbon atoms, and particularly preferably 3 to 8 carbon atoms. Preferred specific examples of the cycloalkyl group include cyclopropyl, cyclopentyl, and cyclohexyl.

The acyl group that can be used as R$^{1a}$ preferably has 2 to 40 carbon atoms, more preferably 2 to 30 carbon atoms, still more preferably 2 to 20 carbon atoms, and particularly preferably 2 to 18 carbon atoms.

The aryl group that can be used as R$^{1a}$ preferably has 6 to 20 carbon atoms, more preferably 6 to 15 carbon atoms, still more preferably 6 to 12 carbon atoms, and particularly preferably 6 to 10 carbon atoms. Preferred specific examples of the aryl group include phenyl and naphthyl, among which phenyl is even still more preferable.

The unsaturated aliphatic group that can be used as R$^{1a}$ preferably has 1 to 5 carbon-carbon unsaturated bonds, more preferably 1 to 3 carbon-carbon unsaturated bonds, still more preferably 1 or 2 carbon-carbon unsaturated bond, and particularly preferably 1 carbon-carbon unsaturated bond. The unsaturated aliphatic group may contain a heteroatom, and is also preferably a hydrocarbon group. In a case where the unsaturated aliphatic group is a hydrocarbon group, the number of carbon atoms in the group is preferably 2 to 20, more preferably 2 to 15, still more preferably 2 to 10, even still more preferably 2 to 8, and is also preferably 2 to 5. The unsaturated aliphatic group is more preferably an alkenyl group or an alkynyl group.

R$^{1a}$ is preferably a hydrogen atom, an alkyl group, a cycloalkyl group, or an aryl group, and more preferably an alkyl group or a cycloalkyl group.

In a case where the compound of General Formula (1) has two or more R$^{1a}$'s, the two R$^{1a}$'s may be linked to each other to form a ring.

R$^{2a}$ represents a hydrogen atom, an alkyl group, a cycloalkyl group, an acyl group, an alkenyl group, an aryl group, a phosphonate group (phosphonic acid group), or —SO$_2$R$^{S1}$. R$^{S1}$ represents a substituent.

The alkyl group, cycloalkyl group, acyl group, and aryl group that can be used as R$^{2a}$ have the same definition as the alkyl group, cycloalkyl group, acyl group, and aryl group that can be used as R$^{1a}$, respectively, and a preferred form of each group is also the same as in R$^{1a}$. In addition, the alkyl group that can be used as R$^{2a}$ preferably has an amino group as a substituent.

The alkenyl group that can be used as R$^{2a}$ includes a linear alkenyl group and a branched alkenyl group. The number of carbon atoms in the alkenyl group is preferably 2 to 18, more preferably 2 to 7, and still more preferably 2 to 5. Preferred specific examples of the alkenyl group include vinyl, allyl, butenyl, pentenyl, and hexenyl. The alkenyl group is preferably a substituted alkenyl group.

The phosphonate group that can be used as $R^{2a}$ is a group represented by $—P(=O)(—OR^{P1})OR^{P2}$. $R^{P1}$ and $R^{P2}$ represent a hydrogen atom or a substituent, and the substituent is preferably an alkyl group or a phosphonate group. The alkyl group that can be used as $R^{P1}$ and $R^{P2}$ has the same definition as the alkyl group that can be used as $R^{1a}$ described above, and a preferred form of the alkyl group is also the same as in $R^{1a}$. The phosphonate group that can be used as $R^{P1}$ and $R^{P2}$ has the same definition as the phosphonate group that can be used as $R^{2a}$, and a preferred form thereof is also the same as in $R^{2a}$. In a case where $R^{P1}$ or $R^{P2}$ is a phosphonate group, the $R^1$ and $R^2$ constituting the phosphonate group are each preferably an alkyl group.

As to the phosphonate group that can be used as $R^{2a}$, it is preferable that both $R^{P1}$ and $R^{P2}$ are alkyl groups, or $R^{P1}$ is a hydrogen atom and $R^{P2}$ is a phosphonate group.

Since the phosphonate group is tautomeric with a phosphite group (phosphorous acid group), the phosphonate group in the present invention means to include the phosphite group.

In $—SO_2R^{S1}$ that can be used as $R^{2a}$, the substituent $R^{S1}$ is preferably an alkyl group or an aryl group. Preferred forms of the alkyl group and aryl group that can be used as $R^{S1}$ include the above-described preferred forms of the alkyl group and aryl group that can be used as $R^{1a}$, respectively. Among these, phenyl having an alkyl group as a substituent is preferable for $R^{S1}$. A preferred form of the alkyl group is the same as the above-described preferred form of the alkyl group that can be used as $R^{1a}$.

In a case where the compound represented by General Formula (1) has two or more $R^{2a}$'s, the two $R^{2a}$'s may be linked to each other to form a ring.

m1 is an integer of 0 to 2.

In General Formula (1), it is preferable that at least one of $OR^{2a}$'s has an acetonato structure. The acetonato structure means a structure that one hydrogen ion is removed from acetone or a compound having a structure in which acetone has a substituent, and then the resultant is coordinated to Al. A coordinating atom coordinated to the Al is usually an oxygen atom. The acetonato structure is preferably a structure in which an acetylacetone structure ("$CH_3-C(=O)—CH_2-C(=O)—CH_3$") is taken as a basic structure, one hydrogen ion is removed from the structure, and the structure is coordinated to Al through an oxygen atom as a coordinating atom (that is, an acetylacetonato structure). The phrase "an acetylacetone structure is taken as a basic structure" means to include a structure in which a hydrogen atom of the acetylacetone structure is substituted with a substituent, in addition to the above-described acetylacetone structure. Examples of the form in which $OR^{2a}$ has an acetonato structure include compounds SL-2 and SL-3, which will be described later.

In General Formula (1), it is preferable that at least one of $OR^{2a}$'s has an acetato structure. In the present invention, the acetato structure means a structure that one hydrogen ion is removed from acetic acid or an acetic acid ester, or a compound having a structure in which the acetic acid or acetic acid ester has a substituent (including a form in which the methyl group of acetic acid has an alkyl group as a substituent), and then the resultant is coordinated to Al. A coordinating atom coordinated to the Al is usually an oxygen atom. The acetato structure is preferably a structure in which an alkylacetoacetato structure ("$CH_3-C(=O)—CH_2-C(=O)—O—R_{alk}$" ($R_{alk}$ represents an alkyl group (preferably an alkyl group having 1 to 20 carbon atoms, may be an alkyl group having 1 to 10 carbon atoms, and more preferably an alkyl group having 1 to 4 carbon atoms))) is taken as a basic structure, one hydrogen ion is removed from the structure, and the structure is coordinated to Al through an oxygen atom as a coordinating atom (that is, an alkylacetoacetato structure). The phrase "an alkylacetoacetato structure is taken as a basic structure" means to include a structure in which a hydrogen atom of the alkylacetoacetato structure is substituted with a substituent, in addition to the above-described alkylacetoacetato structure. Examples of the form in which $OR^{2a}$ has an acetato structure include compounds SL-3, SL-4, and SL-5, which will be described later.

The group that can be used as $R^{1a}$ or $R^{2a}$ may have an anionic group having a counter cation (salt-type substituent) as a substituent. The anionic group means a group capable of forming an anion. Examples of the anionic group having a counter cation include a carboxylic acid ion group having an ammonium ion as a counter cation. In this case, the counter cation may be present in the compound represented by General Formula (1) such that a charge of the entire compound is zero. This also applies to a compound represented by General Formula (2) and a compound represented by General Formula (3), which will be described later.

Hereinafter, specific examples of the aluminum alkoxide compound used in the present invention will be given, but the present invention is not limited thereto.

Aluminum triethylate
Aluminum triisopropylate
Aluminum tri-sec-butyrate
Aluminum tris(ethylacetoacetate)
Ethyl acetoacetate aluminum diisopropylate
Aluminum monoacetylacetonate bis(ethylacetoacetate)
Aluminum tris(acetylacetonate)
Diisopropoxy aluminum-9-octadecenylacetoacetate
Aluminum diisopropoxy monoethylacetoacetate
Aluminum tris(ethylacetoacetate)
Aluminum tris(acetylacetonate)
Mono sec-butoxyaluminum diisopropylate
Diethylacetoacetate aluminum isopropylate
Aluminum bis(ethylacetoacetate) monoacetylacetonate
Aluminum octadecylacetoacetate diisopropylate (Zirconium Alkoxide Compound)

The zirconium alkoxide compound preferably includes at least one kind of an acetonato structure, an acetato structure, or a lactato structure, and more preferably includes at least one kind of an acetonato structure or an acetato structure.

The zirconium alkoxide compound preferably includes at least one compound represented by General Formula (2).

$$R^{1b}{}_{m2}\text{-Zr}—(OR^{2b})_{4-m2} \quad \text{General Formula (2):}$$

$R^{1b}$ represents a hydrogen atom, an alkyl group, a cycloalkyl group, an acyl group, an aryl group, or an unsaturated aliphatic group.

As the alkyl group, the cycloalkyl group, the acyl group, the aryl group, and the unsaturated aliphatic group, for example, an alkyl group, a cycloalkyl group, an acyl group, an aryl group, and an unsaturated aliphatic group that can be used as $R^{1a}$ of General Formula (1) can be adopted.

$R^{2b}$ represents a hydrogen atom, an alkyl group, a cycloalkyl group, an acyl group, an alkenyl group, an aryl group, a phosphonate group, or $—SO_2R^{S2}$. $R^{S2}$ represents a substituent.

As the alkyl group, the cycloalkyl group, the acyl group, the alkenyl group, the aryl group, and the phosphonate group, for example, an alkyl group, a cycloalkyl group, an acyl group, an alkenyl group, an aryl group, and a phosphonate group that can be used as $R^{2a}$ of General Formula (1) can be adopted. In addition, as the substituent that can be used as $R^{S2}$, for example, a substituent that can be used as $R^{S1}$ of General Formula (1) can be adopted.

m2 is an integer of 0 to 3.

In General Formula (2), it is preferable that at least one of $OR^{2b}$'s has an acetonato structure. The acetonato structure has the same definition as the acetonato structure described by General Formula (1). Examples of the form in which $OR^{2b}$ has an acetonato structure include compounds SZ-3 and SZ-6, which will be described later.

In addition, in General Formula (2), it is preferable that at least one of $OR^{2b}$'s has an acetato structure. The acetato structure has the same definition as the acetato structure described by General Formula (1). Examples of the form in which $OR^{2b}$ has an acetato structure include a compound SZ-7 which will be described later. The compound SZ-5 corresponds to the form in which $R^{2b}$ is an acyl group in General Formula (1).

In addition, in General Formula (2), it is preferable that at least one of $OR^{2b}$'s has a lactato structure. The lactato structure means a structure in which a lactic acid ion (lactate) is taken as a basic structure, and one hydrogen ion is removed from the basic structure, and the structure is coordinated to Zr. The phrase "a lactic acid ion is taken as a basic structure" means to include, in addition to the lactic acid ion, a structure in which a hydrogen atom of the lactic acid ion is substituted with a substituent. A coordinating atom coordinated to the Zr is usually an oxygen atom. Examples of the form in which $OR^{2b}$ has a lactato structure include a compound SZ-4 which will be described later.

Hereinafter, specific examples of the zirconium alkoxide compound used in the present invention will be given, but the present invention is not limited thereto.

- Tetrapropoxyzirconium (also known as zirconium tetra-n-propoxide)
- Tetrabutoxyzirconium (also known as zirconium tetra-n-butoxide)
- Zirconium tetraacetylacetonate
- Zirconium tributoxy monoacetylacetonate
- Zirconium dibutoxy bis(acetyl acetonate)
- Zirconium dibutoxy bis(ethyl acetoacetate)
- Zirconium tributoxyethylacetoacetate
- Zirconium monobutoxyacetylacetonate bis(ethyl acetoacetate)
- Zirconium tributoxy monostearate (also known as zirconium stearate tri-n-butoxide)
- Zirconium stearate
- Zirconium lactate ammonium salt
- Zirconium monoacetylacetonate (Titanium Alkoxide Compound)

It is preferable that the titanium alkoxide compound includes at least one atom of N, P, or S. In addition, it is also preferable that the titanium alkoxide compound has an acetato structure.

The titanium alkoxide compound preferably includes at least one compound represented by General Formula (3).

$$R^{1c}_{m3}\text{-Ti—}(OR^{2c})_{4-m3} \qquad \text{General Formula (3):}$$

$R^{1c}$ represents a hydrogen atom, an alkyl group, a cycloalkyl group, an acyl group, an aryl group, or an unsaturated aliphatic group.

As the alkyl group, the cycloalkyl group, the acyl group, the aryl group, and the unsaturated aliphatic group, for example, an alkyl group, a cycloalkyl group, an acyl group, an aryl group, and an unsaturated aliphatic group that can be used as $R^{1a}$ of General Formula (1) can be adopted.

$R^{2c}$ represents a hydrogen atom, an alkyl group, a cycloalkyl group, an acyl group, an alkenyl group, an aryl group, a phosphonate group, or $—SO_2R^{S3}$. $R^{S3}$ represents a substituent.

As the alkyl group, the cycloalkyl group, the acyl group, the alkenyl group, the aryl group, and the phosphonate group, for example, an alkyl group, a cycloalkyl group, an acyl group, an alkenyl group, an aryl group, and a phosphonate group that can be used as $R^{2a}$ of General Formula (1) can be adopted. In addition, as the substituent that can be used as $R^{S3}$, for example, a substituent that can be used as $R^{S1}$ of General Formula (1) can be adopted.

m3 is an integer of 0 to 3.

The compound represented by General Formula (3) preferably contains at least one atom of N, P, or S. In a case where the compound represented by General Formula (3) has N, it is preferable to have the N as an amino group.

In a case where the compound represented by General Formula (3) has P, it is preferable to have the P as a phosphate group (phosphoric acid group) or a phosphonate group (phosphonic acid group).

In a case where the compound represented by General Formula (3) has S, it is preferable to have the S as a sulfonyl group ($—SO_2—$).

In addition, it is also preferable that the compound represented by General Formula (3) has an acyl group as $R^{2c}$, that is, has the above-described acetato structure as $OR^{2c}$.

Hereinafter, specific examples of the titanium alkoxide compound used in the present invention will be given, but the present invention is not limited thereto.

- Isopropyltriisostearoyl titanate
- Isopropyltridodecylbenzenesulfonyl titanate
- Isopropyltrioctanoyl titanate
- Isopropyltri(dioctylphosphite)titanate
- Isopropyltris(dioctylpyrophosphate)titanate
- Isopropyltri(dioctylsulfate)titanate
- Isopropyltricumylphenyl titanate
- Isopropyltri(N-aminoethyl-aminoethyl)titanate
- Isopropyldimethacryl isostearoyl titanate
- Isopropylisostearoyl diacryl titanate
- Isobutyltrimethyl titanate
- Diisostearoylethylene titanate
- Diisopropyl bis(dioctylpyrophosphate)titanate
- Dioctyl bis(ditridecylphosphate)titanate
- Dicumyl phenyl oxyacetate titanate
- Bis(dioctylpyrophosphate)oxyacetate titanate
- Bis(dioctylpyrophosphate)ethylene titanate
- Tetraisopropyl titanate
- Tetrabutyl titanate
- Tetraoctyl titanate
- Tetrastearyl titanate
- Tetraisopropyl bis(dioctylphosphite)titanate
- Tetraoctyl bis(di-tridecylphosphite)titanate
- Tetra(2,2-diallyloxymethyl-1-butyl)bis(di-tridecyl)phosphite titanate
- Butyl titanate dimer
- Titanium tetraacetylacetonate
- Titanium ethyl acetoacetate
- Titanium octylene glycolate
- Titanium di-2-ethylhexoxybis(2-ethyl-3-hydroxyhexoxide)

A mass ratio of the tungsten carbide particles and the surface treatment agent in the component (C) is not particularly limited, but for example, with respect to 100 parts by mass of the tungsten carbide particles, an amount of the surface treatment agent is preferably 1 to 100 parts by mass, more preferably 1 to 80 parts by mass, and from the viewpoint of suppressing the decrease in acoustic velocity of the acoustic matching sheet and viewpoint of reducing the variations in acoustic characteristics of the acoustic matching sheet, still more preferably 1 to 50 parts by mass, even more preferably 5 to 50 parts by mass, and even still more preferably 10 to 50 parts by mass.

The mass ratio of the tungsten carbide particles and the surface treatment agent in the component (C) has the same meaning as the mass ratio of the amount of the tungsten carbide particles to the amount of the surface treatment agent used in the surface treatment. The mass ratio of the tungsten carbide particles to the surface treatment agent in the component (C) can be calculated from the mass of the tungsten carbide particles and the mass of the component (C) with a thermogravimetric analysis (TGA) or the like by heating the component (C) to 500° C. or higher to remove an organic component to obtain an inorganic component (tungsten carbide particles).

A surface treatment agent other than the above-described surface treatment agent may be used as long as the effects of the present invention are not impaired.

The surface treatment method itself can be carried out by a conventional method.

As for the component (C), it is not necessary that the entire surface of the tungsten carbide particles is treated with the surface treatment agent. For example, it is preferable that 50% or more of 100% surface area of the tungsten carbide particles is surface-treated, more preferable that 70% or more thereof is surface-treated, and still more preferable that 90% or more thereof is surface-treated.

The component (C) may be used alone or in combination of two or more thereof.

From the viewpoint of increasing the acoustic impedance, a content of the component (C) in the total of 100 parts by mass of each content of the components (A) to (C) is preferably 60 parts by mass or more, more preferably 70 parts by mass or more, still more preferably 80 parts by mass or more, and even more preferably 90 parts by mass or more. In addition, the content of the component (C) in the total of 100 parts by mass of each content of the components (A) to (C) is preferably 98 parts by mass or less, more preferably 95 parts by mass or less, and still more preferably 94 parts by mass or less. By setting the content of the component (C) to 90 parts by mass or more and 94 parts by mass or less, the variations in acoustic characteristics can be effectively suppressed.

In addition, the contents of the components (A) and (B) in the total of 100 parts by mass of each content of the components (A) to (C) is preferably in the following range.

The content of the component (A) is preferably 1 part by mass or more, more preferably 2 parts by mass or more, and still more preferably 4 parts by mass or more. In addition, it is preferably 10 parts by mass or less, more preferably 9 parts by mass or less, and still more preferably 8 parts by mass or less.

The content of the component (B) is preferably 0.05 parts by mass or more, more preferably 0.1 parts by mass or more, and still more preferably 0.14 parts by mass or more. In addition, it is preferably 4 parts by mass or less, more preferably 3 parts by mass or less, and still more preferably 2.5 parts by mass or less.

A content ratio of the component (A) and the component (B) may be appropriately adjusted according to the type of the component (B) to be used, and the like. For example, in terms of a mass ratio, component (A)/component (B) can be 99/1 to 20/80, preferably 90/1 to 40/60 and more preferably 90/1 to 75/25.

<Surface Modification Step>

In addition, from the viewpoint of suppressing the decrease in acoustic velocity of the acoustic matching sheet and viewpoint of reducing the variations in acoustic characteristics of the acoustic matching sheet, before the surface treatment with the above-described surface treatment agent, the surface-treated tungsten carbide particles used in the present invention may be subjected to a surface modification by contacting the tungsten carbide particles with an oxidant in an aqueous solution.

The surface modification step is a step of contacting the tungsten carbide particles with an oxidant in an aqueous solution to obtain modified tungsten carbide particles.

A pH of the above-described aqueous solution is, for example, more than 7, preferably 10 or more, more preferably 12 or more, still more preferably more than 12, particularly preferably 13 or more, and most preferably more than 13.

The upper limit of the pH of the above-described aqueous solution is not limited, and is, for example, 14 or less.

The pH of the above-described aqueous solution means the pH of the above-described aqueous solution in a state including the above-described tungsten carbide particles and the above-described oxidant. That is, the above-described aqueous solution includes at least water, the tungsten carbide particles, and the oxidant.

A time for contacting the tungsten carbide particles with the oxidant in the above-described aqueous solution is preferably 0.1 to 24 hours, more preferably 0.5 to 10 hours, and still more preferably 1.5 to 6 hours.

In addition, a temperature of the above-described aqueous solution in a case of contacting the tungsten carbide particles with the oxidant is preferably 1° C. to 95° C., more preferably 25° C. to 80° C., and still more preferably 45° C. to 65° C.

A method for contacting the tungsten carbide particles with the oxidant in the above-described aqueous solution is not limited, and examples thereof include a method of mixing and contacting by processing using a pulverizer or crusher such as rocking mill, bead mill, ball mill, Henschel mixer, jet mill, starburst, and paint conditioner, a method of contacting while stirring using a mechanical stirrer such as a three-one motor and a magnetic stirrer, and a method of contacting a cartridge filled with the tungsten carbide particles while circulating an oxidant aqueous solution including the oxidant and the like with a pump.

In addition, as the method for contacting the tungsten carbide particles with the oxidant in the above-described aqueous solution, a method which does not destroy the tungsten carbide particles or the modified tungsten carbide particles as much as possible in the above-described aqueous solution may be selected. The term "destroy" as used herein means that, for example, in a case where the tungsten carbide particles to be treated are aggregated tungsten carbide particles, the aggregated morphology is destroyed.

It is preferable to contact the tungsten carbide particles with the oxidant in the above-described aqueous solution, and then take out the obtained modified tungsten carbide particles from the above-described aqueous solution.

A method for taking out the modified tungsten carbide particles from the above-described aqueous solution is not limited, and examples thereof include a method of filtering the above-described aqueous solution to separate (filter) the modified tungsten carbide particles as a filtered product.

It is also preferable to wash the modified tungsten carbide particles to be taken out with water and/or an organic solvent or the like.

(Oxidant)

The above-described aqueous solution includes an oxidant.

The oxidant is not limited, and examples thereof include persulfates such as sodium persulfate, potassium persulfate, and ammonium persulfate; nitrates such as ammonium cerium nitrate, sodium nitrate, and ammonium nitrate; peroxides such as hydrogen peroxide and tert-butyl hydroperoxide; permanganates such as potassium permanganate; divalent copper compounds and transition metal compounds; hypervalent iodine compounds such as potassium periodate and sodium periodate; quinone compounds such as benzoquinone, naphthoquinone, anthraquinone, and chloranil; and hydrogen oxyacid salts such as sodium hypochlorite and sodium chlorite.

Among these, the oxidant preferably includes a persulfate, and is more preferably a persulfate.

In addition, in order to assist the action of the oxidant, a catalyst may be used in addition to the oxidant. Examples of the above-described catalyst include a divalent iron compound ($FeSO_4$ and the like) and a trivalent iron compound.

The oxidant and/or the catalyst may be a hydrate.

In addition, a standard oxidation-reduction potential of the oxidant is preferably 0.30 V or more, more preferably 1.50 V or more, and still more preferably 1.70 V or more. The upper limit of the standard oxidation-reduction potential of the oxidant is not limited, and for example, is preferably 4.00 V or less and more preferably 2.50 V or less.

The above-described standard oxidation-reduction potential is based on a standard hydrogen electrode.

A content of the oxidant in the above-described aqueous solution is preferably 0.05 to 20 parts by mass, more preferably 0.1 to 20 parts by mass, and still more preferably 1 to 20 parts by mass with respect to 100 parts by mass of water in the above-described aqueous solution.

The oxidant may be used alone or in combination of two or more kinds thereof.

In a case where the above-described aqueous solution includes a catalyst, a content thereof is preferably 0.005 to 2 parts by mass, more preferably 0.01 to 2 parts by mass, and still more preferably 0.1 to 2 parts by mass with respect to 100 parts by mass of water in the above-described aqueous solution.

The content of the catalyst in the above-described aqueous solution is preferably 0.1 to 80 parts by mass, more preferably 1 to 50 parts by mass, and still more preferably 5 to 20 parts by mass with respect to 100 parts by mass of the oxidant in the above-described aqueous solution.

The catalyst may be used alone or in combination of two or more kinds thereof.

In addition, the amount of the oxidant contact with the tungsten carbide particles is preferably 0.1 to 1000 parts by mass, more preferably 1 to 250 parts by mass, and still more preferably 15 to 120 parts by mass with respect to 100 parts by mass of the tungsten carbide particles.

(Alkaline Source)

In order to adjust the pH of the above-described aqueous solution, the above-described aqueous solution also preferably includes an alkaline source in addition to the above-described components.

Examples of the above-described alkaline source include inorganic bases such as an alkali metal hydroxide (sodium hydroxide and the like) and an alkaline earth metal hydroxide; and organic bases.

A content of the alkaline source in the above-described aqueous solution may be appropriately adjusted such that the pH of the above-described aqueous solution can be adjusted to a desired pH, but for example, the content thereof is 0.1 to 10 parts by mass with respect to 100 parts by mass of water in the above-described aqueous solution.

<Other Components>

In addition to the components (A) to (C), examples of the material according to the embodiment of the present invention include a curing retarder, a dispersant, a pigment, a dye, an antistatic agent, an antioxidant, a flame retardant, and a thermal conductivity improver.

<Preparation of Material for Acoustic Matching Layer>

In a case where the material according to the embodiment of the present invention is in the form of a composition for an acoustic matching layer in which the components (A) to (C) are mixed, a mixing method is not particularly limited as long as each component can be mixed substantially uniformly. For example, a desired uniform mixing can be achieved by kneading using a rotation and revolution stirrer. An acoustic matching sheet or a precursor thereof can be prepared by curing this mixture while molding the mixture.

In addition, in a case where the material according to the embodiment of the present invention is in the form of a set for an acoustic matching layer, which includes a main agent including the components (A) and (C) and the curing agent of the component (B) (corresponding to the above-described aspect (ii)), the main agent can be obtained by mixing the component (A) and the component (C). An acoustic matching sheet or a precursor thereof can be prepared by mixing the main agent and the curing agent during production of the acoustic matching sheet, and mixing this mixture while molding the mixture.

[Acoustic Matching Sheet (Acoustic Matching Layer)]

An acoustic matching sheet according to an embodiment of the present invention can be obtained by molding a mixture of the above-described respective components, curing the mixture, and then cutting, dicing or the like to a desired thickness or shape, if necessary. In addition, the acoustic matching sheet can be further processed into a desired shape by a conventional method.

Specifically, for example, the material according to the embodiment of the present invention is shaped into a desired sheet in a low temperature region where a curing reaction does not occur or in a low temperature region where a curing rate is sufficiently slow. Next, if necessary, the sheet is cured by heating or the like to obtain a cured substance, and this cured substance is cut or diced to a desired thickness or shape as necessary to obtain an acoustic matching sheet. That is, the acoustic matching sheet to be formed is preferably a cured substance obtained by curing a mixture of the respective components constituting the material according to the embodiment of the present invention. This acoustic matching sheet is used as an acoustic matching layer of an acoustic wave probe. The configuration of the acoustic wave probe including the acoustic matching layer will be described later.

[Acoustic Wave Probe]

An acoustic wave probe according to an embodiment of the present invention includes the acoustic matching sheet according to the embodiment of the present invention as at least one layer of an acoustic matching layer.

An example of the configuration of the acoustic wave probe according to the embodiment of the present invention is shown in FIG. 1. The acoustic wave probe shown in FIG. 1 is an ultrasound probe in an ultrasound diagnostic apparatus. The ultrasound probe is a probe which particularly uses an ultrasonic wave as an acoustic wave in an acoustic wave probe. Therefore, a basic structure of the ultrasound probe can be applied to the acoustic wave probe as it is.

<Ultrasound Probe>

An ultrasound probe 10 is a main component of the ultrasound diagnostic apparatus and has a function of generating an ultrasonic wave and transmitting and receiving an ultrasonic beam. As shown in FIG. 1, a configuration of the ultrasound probe 10 is provided in the order of an acoustic lens 1, an acoustic matching layer 2, a piezoelectric element layer 3, and a backing material 4 from a distal end portion (surface coming into contact with a living body which is a test object). In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

(Piezoelectric Element Layer)

The piezoelectric element layer 3 is a portion which generates an ultrasonic wave and in which an electrode is attached to both sides of a piezoelectric element. In a case where voltage is applied to the electrode, the piezoelectric element layer 3 generates an ultrasonic wave through repeated contraction and expansion of the piezoelectric element and through vibration.

A so-called ceramics inorganic piezoelectric body obtained by a polarization treatment of quartz crystals, single crystals such as $LiNbO_3$, $LiTaO_3$, and $KNbO_3$, thin films of ZnO and AlN, $Pb(Zr, Ti)O_3$-based sintered body, and the like is widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent wideband characteristics, and excellent mass productivity and has less characteristic variations, is obtained is disclosed in JP2011-071842A or the like.

In the present invention, it is possible to preferably use any piezoelectric element material.

(Backing Material)

The backing material 4 is provided on a rear surface of the piezoelectric element layer 3 and contributes to the improvement in distance resolution in an ultrasound diagnostic image by shortening the pulse width of an ultrasonic wave through the suppression of excess vibration.

(Acoustic Matching Layer)

The acoustic matching layer 2 is provided in order to reduce the difference in acoustic impedance between the piezoelectric element layer 3 and a test object and to efficiently transmit and receive an ultrasonic wave.

(Acoustic Lens)

The acoustic lens 1 is provided to focus an ultrasonic wave in a slice direction by utilizing refraction to improve the resolution. In addition, it is necessary for the acoustic lens 1 to achieve matching of an ultrasonic wave with the acoustic impedance (1.4 to 1.7 Mrayl in a case of a human body) of a living body which is a test object after being closely attached to the living body and to reduce the amount of ultrasonic attenuation of the acoustic lens 1 itself.

That is, by using, as the material of the acoustic lens 1, a material in which the acoustic velocity is sufficiently lower than the acoustic velocity of the human body, the attenuation of ultrasonic wave is small, and the acoustic impedance is close to the value of the skin of the human body, sensitivity of transmission and reception of the ultrasonic wave is increased.

The operation of the ultrasound probe 10 having such a configuration will be described. The piezoelectric element layer 3 is resonated after applying a voltage to the electrodes provided on both sides of the piezoelectric element, and an ultrasonic signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

[Manufacturing of Acoustic Wave Probe]

The acoustic wave probe according to the embodiment of the present invention can be produced by a conventional method, except that the material according to the embodiment of the present invention is used. That is, the method for manufacturing an acoustic wave probe according to the embodiment of the present invention includes forming an acoustic matching layer on a piezoelectric element side using the material according to the embodiment of the present invention. The piezoelectric element can be provided on the backing material by a conventional method.

In addition, an acoustic lens is formed on the acoustic matching layer by a conventional method using a material for forming an acoustic lens.

[Acoustic Wave Measurement Apparatus]

An acoustic wave measurement apparatus according to an embodiment of the present invention includes the acoustic wave probe according to the embodiment of the present invention. The acoustic wave measurement apparatus has a function of displaying the signal intensity of a signal received by the acoustic wave probe and imaging the signal.

It is also preferable that the acoustic wave measurement apparatus according to the embodiment of the present invention is an ultrasonic diagnostic apparatus using an ultrasound probe.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

[Preparation Example] Preparation Example of Surface-Treated Tungsten Carbide Particles (C-1)

3.0 parts by mass of 3-aminopropyltrimethoxysilane, 100 parts by mass of methanol, and 3.3 parts by mass of distilled water were mixed and then allowed to stand at 23° C. for 1 hour to proceed with a hydrolysis of the methoxy group. 10.0 parts by mass of tungsten carbide particles (manufactured by A.L.M.T. Corp., trade name: "WC60S", average primary particle diameter: 6.5 μm) was added to this solution. Using a homogenizer ("EXCEL AUTO HOMOGENIZER ED-7" (trade name), manufactured by Nippon Seiki Co., Ltd.), the mixture was stirred at a rotation speed of 10,000 rpm for 60 minutes while cooling such that the liquid temperature did not exceed 50° C., and a surface treatment was carried out while pulverizing.

The mixture after stirring and pulverizing above was filtered off, and the obtained solid was heated and dried at 100° C. for 30 minutes to obtain powdery surface-treated tungsten carbide particles (C-1) (component (C)).

Surface-treated tungsten carbide particles (C-2) to (C-30) were prepared in the same manner as the surface-treated tungsten carbide particles (C-1), except that, in the preparation of the surface-treated tungsten carbide particles (C-1), the raw materials were used in the compositions shown in Table 1 below. The following tables 1-1 to 1-6 are collectively referred to as Table 1.

In the preparation of the surface-treated tungsten carbide particles (C-2) to (C-30), 10.0 parts by mass of tungsten carbide particles as a raw material was used.

In the preparation of the surface-treated tungsten carbide particles (C-1), in a case where tungsten particles were used instead of the tungsten carbide particles, the surface could not be sufficiently treated and the particles aggregated, so that it could not be used.

[Preparation Example] Preparation Example of Surface-Treated Tungsten Carbide Particles (C-31)

Tungsten carbide particles (50 g) was added to NaOH water (NaOH: 40 g/water: 400 ml) and stirred. Sodium persulfate water (sodium persulfate: 9.6 g/water: 100 ml) was further added to the above-described NaOH water, the above-described NaOH water was heated to 50° C. and further stirred for 3 hours (modification step). A three-one motor manufactured by Shinto Scientific Co., Ltd. was used for the stirring, and the stirring was performed at 150 rpm.

After cooling the above-described NaOH water to room temperature, the tungsten carbide particles in the above-described NaOH water were collected by filtration, and the collected tungsten carbide particles were washed with water (500 ml) and acetonitrile (250 ml) to obtain modified tungsten carbide particles.

Surface-treated tungsten carbide particles (C-31) were prepared in the same manner as the surface-treated tungsten carbide particles (C-1), except that, in the preparation of the surface-treated tungsten carbide particles (C-1), the modified tungsten carbide particles were used instead of the tungsten carbide particles.

Surface-treated tungsten carbide particles (C-32) to (C-48) were prepared in the same manner as the surface-treated tungsten carbide particles (C-31), except that, in the preparation of the surface-treated tungsten carbide particles (C-31), the raw materials were used in the compositions shown in Table 1 below.

TABLE 1

Table 1-1

| | | C-1 | C-2 | C-3 | C-4 | C-5 | C-6 | C-7 | C-8 | C-9 | C-10 |
|---|---|---|---|---|---|---|---|---|---|---|---|
| Tungsten carbide (W) | Type | W-2 | W-2 | W-2 | W-2 | W-2 | W-2 | W-2 | W-2 | W-2 | W-2 |
| | Particle diameter [μm] | 6.5 | 6.5 | 6.5 | 6.5 | 6.5 | 6.5 | 6.5 | 6.5 | 6.5 | 6.5 |
| Surface treatment agent (S) | Type | SA-1 | SA-2 | SM-1 | SM-2 | SI-1 | SI-2 | ST-1 | ST-2 | ST-3 | SL-1 |
| | Number of acetonato structures | — | — | — | — | — | — | — | — | — | — |
| | Number of acetato structures | — | — | — | — | — | — | — | — | — | — |
| | Used amount [part by mass] | 20 | 20 | 20 | 20 | 20 | 20 | 20 | 20 | 20 | 20 |

Table 1-2

| | | C-11 | C-12 | C-13 | C-14 | C-15 | C-16 | C-17 | C-18 | C-19 | C-20 |
|---|---|---|---|---|---|---|---|---|---|---|---|
| Tungsten carbide (W) | Type | W-2 | W-2 | W-2 | W-2 | W-2 | W-2 | W-2 | W-2 | W-2 | W-2 |
| | Particle diameter [μm] | 6.5 | 6.5 | 6.5 | 6.5 | 6.5 | 6.5 | 6.5 | 6.5 | 6.5 | 6.5 |
| Surface treatment agent (S) | Type | SL-2 | SL-3 | SL-4 | SL-5 | SZ-1 | SZ-2 | SZ-3 | SZ-4 | SZ-5 | SZ-6 |
| | Number of acetonato structures | 3 | 1 | — | — | — | — | 4 | — | — | 1 |
| | Number of acetato structures | — | 2 | 3 | 1 | — | — | — | — | — | — |
| | Used amount [part by mass] | 20 | 20 | 20 | 20 | 20 | 20 | 20 | 20 | 20 | 20 |

Table 1-3

| | | C-21 | C-22 | C-23 | C-24 | C-25 | C-26 | C-27 | C-28 | C-29 | C-30 |
|---|---|---|---|---|---|---|---|---|---|---|---|
| Tungsten carbide (W) | Type | W-2 | W-1 | W-3 | W-4 | W-2 | W-2 | W-2 | W-2 | W-2 | W-2 |
| | Particle diameter [μm] | 6.5 | 3 | 9 | 15 | 6.5 | 6.5 | 6.5 | 6.5 | 6.5 | 6.5 |
| Surface treatment agent (S) | Type | SZ-7 | ST-2 | ST-2 | ST-2 | ST-2 | ST-2 | ST-2 | SC-1 | SC-2 | SC-3 |
| | Number of acetonato structures | — | — | — | — | — | — | — | — | — | — |
| | Number of acetato structures | 2 | — | — | — | — | — | — | — | — | — |
| | Used amount [part by mass] | 20 | 20 | 20 | 20 | 10 | 50 | 70 | 20 | 20 | 20 |

TABLE 2

Table 1-4

| | | C-31 | C-32 | C-33 | C-34 | C-35 | C-36 |
|---|---|---|---|---|---|---|---|
| Tungsten carbide (W) | Type | W-2 | W-2 | W-2 | W-2 | W-2 | W-2 |
| | Particle diameter [μm] | 6.5 | 6.5 | 6.5 | 6.5 | 6.5 | 6.5 |
| Surface modification | Type of Oxidant | Sodium persulfate | Sodium persulfate | Sodium persulfate | Sodium persulfate | Sodium persulfate | Sodium persulfate |
| | Standard oxidation-reduction potential [V] | 2.01 | 2.01 | 2.01 | 2.01 | 2.01 | 2.01 |
| Surface treatment agent | Type | SA-1 | SM-1 | SM-2 | SI-1 | SI-2 | ST-1 |
| | Number of acetonato structures | — | — | — | — | — | — |
| | Number of acetato structures | — | — | — | — | — | — |
| | Used amount [part by mass] | 20 | 20 | 20 | 20 | 20 | 20 |

Table 1-5

| | | C-37 | C-38 | C-39 | C-40 | C-41 | C-42 |
|---|---|---|---|---|---|---|---|
| Tungsten carbide (W) | Type | W-2 | W-2 | W-2 | W-2 | W-2 | W-2 |
| | Particle diameter [μm] | 6.5 | 6.5 | 6.5 | 6.5 | 6.5 | 6.5 |
| Surface modification | Type of Oxidant | Sodium persulfate | Sodium persulfate | Sodium persulfate | Sodium persulfate | Sodium persulfate | Sodium persulfate |
| | Standard oxidation-reduction potential [V] | 2.01 | 2.01 | 2.01 | 2.01 | 2.01 | 2.01 |
| Surface treatment agent | Type | ST-2 | ST-3 | SL-1 | SL-2 | SZ-3 | SZ-4 |
| | Number of acetonato structures | — | — | — | — | — | — |
| | Number of acetato structures | — | — | — | — | — | — |
| | Used amount [part by mass] | 20 | 20 | 20 | 20 | 20 | 20 |

Table 1-6

| | | C-43 | C-44 | C-45 | C-46 | C-47 | C-48 |
|---|---|---|---|---|---|---|---|
| Tungsten carbide (W) | Type | W-2 | W-2 | W-2 | W-2 | W-2 | W-2 |
| | Particle diameter [μm] | 6.5 | 6.5 | 6.5 | 6.5 | 6.5 | 6.5 |
| Surface modification | Type of Oxidant | Sodium hypochlorite | Sodium hypochlorite | Sodium hypochlorite | Sodium hypochlorite | Sodium hypochlorite | Sodium hypochlorite |
| | Standard oxidation-reduction potential [V] | 1.63 | 1.63 | 1.63 | 1.63 | 1.63 | 1.63 |
| Surface treatment agent | Type | SA-1 | SM-1 | ST-2 | ST-3 | SL-2 | SZ-3 |
| | Number of acetonato structures | — | — | — | — | — | — |
| | Number of acetato structures | — | — | — | — | — | — |
| | Used amount [part by mass] | 20 | 20 | 20 | 20 | 20 | 20 |

<Notes of Table>

[Tungsten carbide particles (W)]

(W-1):

Untreated tungsten carbide particles (manufactured by A.L.M.T. Corp., trade name: "WC30S", average primary particle diameter: 3 μm)

(W-2):

Untreated tungsten carbide particles (manufactured by A.L.M.T. Corp., trade name: "WC60S", average primary particle diameter: 6.5 μm)

(W-3):

Untreated tungsten carbide particles (manufactured by A.L.M.T. Corp., trade name: "WC80S", average primary particle diameter: 9 μm)

(W-4):

Untreated tungsten carbide particles (manufactured by A.L.M.T. Corp., trade name: "WC100S", average primary particle diameter: 15 μm)

[Surface Treatment Agent (S)]

<Aminosilane Compound>

(SA-1):

3-Aminopropyltrimethoxysilane (manufactured by Gelest, Inc., trade name "SIA0611.0")

<Mercaptosilane Compound>

(SM-1):

3-Mercaptopropyltrimethoxysilane (manufactured by Gelest, Inc., trade name "SIM6476.0")

(SM-2):

11-Mercaptoundecyltrimethoxysilane (manufactured by Gelest, Inc., trade name "SIM6480.0")

<Isocyanatosilane Compound>

(SI-1):

3-Isocyanatopropyltrimethoxysilane (manufactured by Gelest, Inc., trade name "SII6456.0")

(SI-2):

Isocyanatomethyltrimethoxysilane (manufactured by Gelest, Inc., trade name "SII6453.8")

<Titanium Alkoxide Compound>

(ST-1):

Isopropyltriisostearoyl titanate (manufactured by Ajinomoto Fine-Techno Co., Inc., trade name "PLENACT TTS"

ST-1

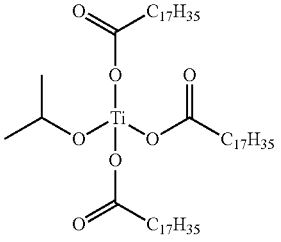

(ST-2):

Dioctyl bis(ditridecylphosphate)titanate ("PLENACT 46B" manufactured by Ajinomoto Fine-Techno Co., Inc.

ST-2

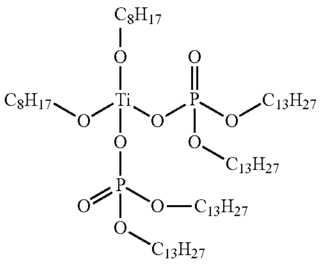

(ST-3):

Isopropyl tri(N-aminoethyl-aminoethyl)titanate (manufactured by Ajinomoto Fine-Techno Co., Inc., trade name "PLENACT 44")

ST-3

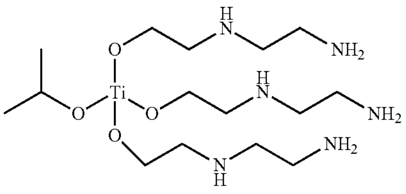

<Aluminum Alkoxide Compound>

(SL-1):

Aluminum tri-sec-butyrate (manufactured by Kawaken Fine Chemicals Co., Ltd., trade name "ASBD")

SL-1

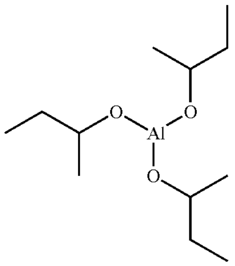

(SL-2):

Aluminum tris(acetylacetonate) (manufactured by Matsumoto Fine Chemical Co., Ltd., trade name "ORGATIX AL-3100")

SL-2

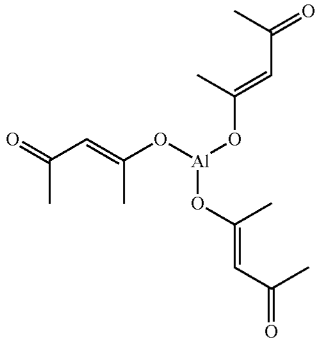

(SL-3):

Aluminum bis(ethylacetoacetate) monoacetylacetonate (manufactured by Matsumoto Fine Chemical Co., Ltd., trade name "ORGATIX AL-3200")

SL-3

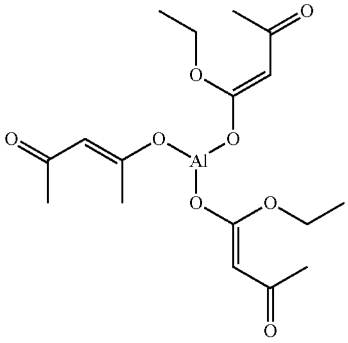

(SL-4):

Aluminum tris(ethylacetoacetate) (manufactured by Matsumoto Fine Chemical Co., Ltd., trade name "ORGATIX AL-3215")

SL-4

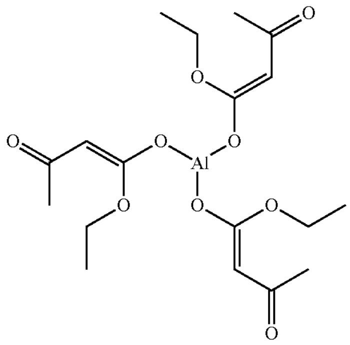

(SL-5):

Aluminum octadecylacetoacetate diisopropylate (manufactured by Ajinomoto Fine-Techno Co., Inc., trade name "PLENACT AL-M")

SL-5

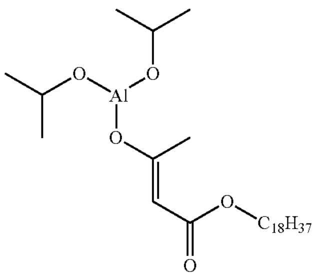

<Zirconium Alkoxide Compound>

(SZ-1):

Zirconium tetra-n-propoxide (manufactured by Matsumoto Fine Chemical Co., Ltd., trade name "ORGATIX ZA-45")

SZ-1

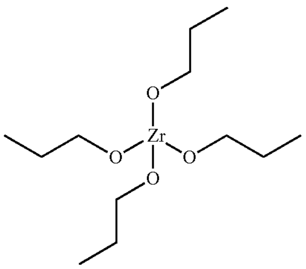

(SZ-2):

Zirconium tetra-n-butoxide (manufactured by Matsumoto Fine Chemical Co., Ltd., trade name "ORGATIX ZA-65")

SZ-2

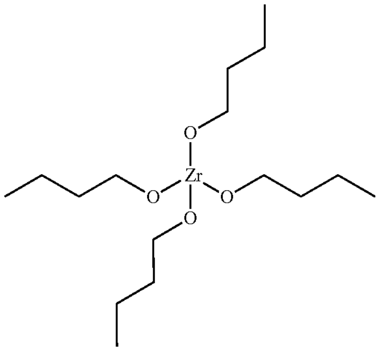

(SZ-3):

Zirconium tetraacetylacetonate (manufactured by Matsumoto Fine Chemical Co., Ltd., trade name "ORGATIX ZC-150")

SZ-3

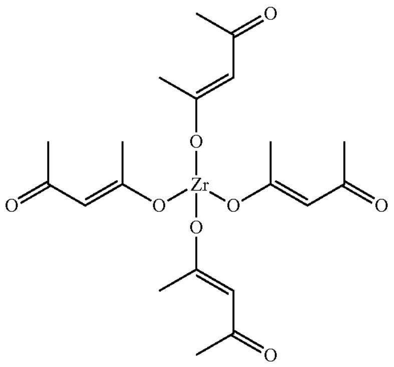

(SZ-4):

Zirconium lactate ammonium salt (manufactured by Matsumoto Fine Chemical Co., Ltd., trade name "ORGATIX ZC-300")

SZ-4

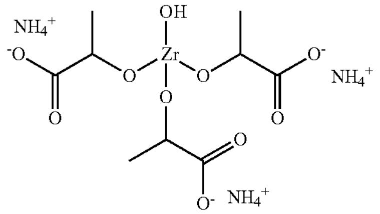

(SZ-5):

Zirconium stearate tri-butoxide (manufactured by Matsumoto Fine Chemical Co., Ltd., trade name "ORGATIX ZC-320")

SZ-5

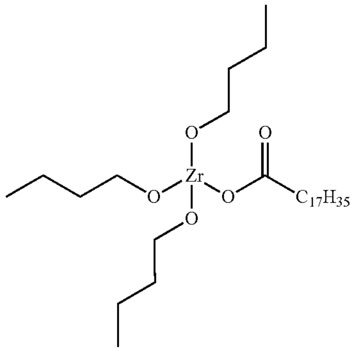

(SZ-6):

Zirconium tributoxy monoacetylacetonate (manufactured by Matsumoto Fine Chemical Co., Ltd., trade name "ORGATIX ZC-540")

SZ-6

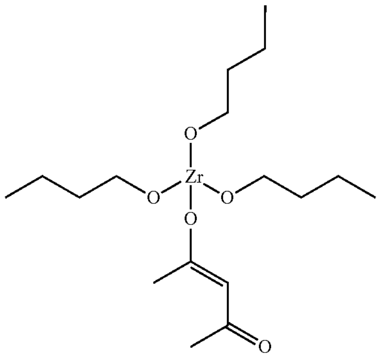

(SZ-7):

Zirconium dibutoxy bis(ethyl acetoacetate) (manufactured by Matsumoto Fine Chemical Co., Ltd., trade name "ORGATIX ZC-580")

SZ-7

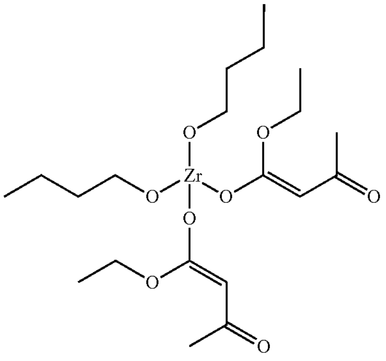

<Oxidant>

Sodium persulfate (manufactured by FUJIFILM Wako Pure Chemical Corporation)

Sodium hypochlorite (manufactured by FUJIFILM Wako Pure Chemical Corporation)

<Surface Treatment Agent Used in Comparative Examples>

(SA-2):

N-trimethoxysilylpropyl-N,N,N-trimethylammonium chloride (manufactured by Gelest, Inc., trade name "SIT8415.0", 50% methanol aqueous solution)

(SC-1):

Methyltrichlorosilane (SC-2):

Vinyltrichlorosilane (SC-3):

3-Methacryloxypropyltrimethoxysilane

<1> Preparation of Material for Acoustic Matching Layer

(1) Preparation of Material for Acoustic Matching Layer Used in Example 1

5.6 parts by mass of an epoxy resin (component (A) in Table 2, bisphenol A diglycidyl ether ("jER825" (trade name) manufactured by Mitsubishi Chemical Corporation, epoxy equivalent: 170)), 1.4 parts by mass of isophorone diamine (component (B) in Table 2), and 93 parts by mass of the surface-treated tungsten carbide particles (C-1) (component (C) in Table 2) prepared in the above-described preparation example were added to a container having a cylindrical inner space having a diameter of 40 mm so that a thickness after mixing was 3 mm, and mixed with a rotation and revolution device (trade name: ARV-310, manufactured by THINKY CORPORATION) to prepare a material for an acoustic matching layer used in Example 1.

(2) Preparation of Materials for Acoustic Matching Layer Used in Examples 2 to 60 and

Comparative Examples 1 to 5

Materials for an acoustic matching layer used in Examples 2 to 60 and Comparative Examples 1 to 5 were prepared in the same manner as in the material for an acoustic matching layer used in Example 1, except that the composition was changed to the composition shown in Table 2 below.

<2> Production of Acoustic Matching Sheet

(1) Production of Acoustic Matching Sheet of Example 1

After mixing the material for an acoustic matching layer used in Example 1, the mixture was stored in the above-described container, and cured at 80° C. for 18 hours and then at 150° C. for 1 hour to produce a circular acoustic matching sheet having a diameter of 40 mm and a thickness of 3 mm. This sheet was cut into three circular acoustic matching sheets having a diameter of 40 mm and a thickness of 1 mm with a dicer, and one acoustic matching sheet (thickness: 1 mm) in the center was used for Test Examples described below.

(2) Production of Acoustic Matching Sheets of Examples 2 to 60 and Comparative Examples 1 to 5

Acoustic matching sheets (thickness: 1 mm) were produced in the same manner as in the acoustic matching sheet used in Example 1, except that the material for an acoustic matching layer used in each of Examples 2 to 60 and Comparative Examples 1 to 5 was used instead of the material for an acoustic matching layer used in Example 1. The produced acoustic matching sheets were used for Test Examples described below.

<3> Production of Reference Acoustic Matching Sheet

A reference acoustic matching sheet used in [Test Example 2] described below was produced as follows.

(1) Production of Reference Acoustic Matching Sheet Used for Evaluation of Example 1

A reference acoustic matching sheet (thickness: 1 mm) used for the evaluation of Example 1 was produced in the same manner as in the acoustic matching sheet used in Example 1, except that, instead of the material for an acoustic matching layer used in Example 1, 80 parts by mass of an epoxy resin (component (A) in Table 2, bisphenol A diglycidyl ether ("jER825" (trade name) manufactured by Mitsubishi Chemical Corporation, epoxy equivalent: 170)) and 20 parts by mass of isophorone diamine (component (B) in Table 2) were used. The produced reference acoustic matching sheets were used for Test Example 2 described below.

(2) Production of Reference Acoustic Matching Sheets Used for Evaluation of Examples 2 to 60 and Comparative Examples 1 to 5

Reference acoustic matching sheets used for the evaluation of Examples 2 to 60 and Comparative Examples 1 to 5 were produced in the same manner as in the production of the reference acoustic matching sheet used for the evaluation of Example 1, except that, in the production of the reference acoustic matching sheet used in Example 1, a formulation ratio of the epoxy resin and the curing agent was changed to a formulation ratio shown in Table 2.

[Test Example 1] Measurement of Acoustic Velocity

The ultrasonic velocity was measured at 25° C. using a sing-around acoustic velocity measurement apparatus (manufactured by Ultrasonic Engineering Co., Ltd., trade name: "UVM-2 model") according to JIS Z2353 (2003). With respect to the circular acoustic matching sheet having a diameter of 40 mm and a thickness of 1 mm obtained above, for three circular regions having a diameter of 1.5 cm that do not overlap one another, the entire inside of these three circular regions (small probe size of a single channel) was measured. The arithmetic mean value of the acoustic velocity in the above three circular regions was calculated, and a proportion (%) of decrease in acoustic velocity obtained from the following expression was applied to the following evaluation standard and evaluated. An evaluation of S to D is acceptable in the present test. The results are shown in Table 2. The following tables 2-1 to 2-7 are collectively referred to as Table 2.

Proportion of decrease in acoustic velocity (%)=100×(Arithmetic mean value of acoustic velocity of reference acoustic matching sheet−Arithmetic mean value of acoustic velocity of acoustic matching sheet of Example or Comparative Example)/Arithmetic mean value of acoustic velocity of reference acoustic matching sheet —Evaluation Standard—

S: less than 5%
A: 5% or more and less than 7%
B: 7% or more and less than 9%
C: 9% or more and less than 11%
D: 11% or more and less than 13%
E: 13% or more and less than 15%
F: 15% or more

[Test Example 2] Variations in Acoustic Impedance (AI)

A 10 mm×10 mm test piece was cut out from each acoustic velocity measurement target (circle with a diameter of 1.5 cm) of Test Example 1 described above. The density of the test piece at 25° C. was measured using an electronic hydrometer (manufactured by Alfa Mirage Co., Ltd., trade name: "SD-200L") in accordance with the density measurement method of Method A (underwater substitution method) described in JIS K7112 (1999). For the acoustic matching sheet of each of Examples and Comparative Examples, the acoustic impedance (density × acoustic velocity) was calculated for each of the three circular regions, and the variations in acoustic characteristics were evaluated by applying them to the following evaluation standard. An evaluation of A to C is acceptable in the present test. The results are shown in Table 2.

—Evaluation Standard—

A: less than 0.5 Mrayl
B: 0.5 Mrayl or more and less than 0.6 Mrayl
C: 0.6 Mrayl or more and less than 0.7 Mrayl
D: 0.7 Mrayl or more and less than 1 Mrayl
E: 1 Mrayl or more

TABLE 3

Table 2-1

| | | EX1 | EX2 | EX3 | EX4 | EX5 | EX6 | EX7 | EX8 | EX9 | EX10 |
|---|---|---|---|---|---|---|---|---|---|---|---|
| Component (A) | Type | A-1 | A-1 | A-1 | A-1 | A-1 | A-1 | A-1 | A-1 | A-1 | A-1 |
| | Content [part by mass] | 5.6 | 5.6 | 5.6 | 5.6 | 5.6 | 5.6 | 5.6 | 5.6 | 5.6 | 5.6 |
| Component (B) | Type | B-1 | B-1 | B-1 | B-1 | B-1 | B-1 | B-1 | B-1 | B-1 | B-1 |
| | Content [part by mass] | 1.4 | 1.4 | 1.4 | 1.4 | 1.4 | 1.4 | 1.4 | 1.4 | 1.4 | 1.4 |
| Component (C) | Type | C-1 | C-3 | C-4 | C-5 | C-6 | C-7 | C-8 | C-9 | C-10 | C-11 |
| | Particle diameter [μm] | 6.5 | 6.5 | 6.5 | 6.5 | 6.5 | 6.5 | 6.5 | 6.5 | 6.5 | 6.5 |
| | Surface treatment agent (S) | SA-1 | SM-1 | SM-2 | SI-1 | SI-2 | ST-1 | ST-2 | ST-3 | SL-1 | SL-2 |

TABLE 3-continued

| | | | | | | | | | | | |
|---|---|---|---|---|---|---|---|---|---|---|---|
| | Treated amount [php] | 20 | 20 | 20 | 20 | 20 | 20 | 20 | 20 | 20 | 20 |
| | Content [part by mass] | 93 | 93 | 93 | 93 | 93 | 93 | 93 | 93 | 93 | 93 |
| Decrease in acoustic velocity | | C | D | D | D | D | A | A | A | C | B |
| Variations in AI | | C | C | C | C | C | B | A | A | B | B |

Table 2-2

| | | EX11 | EX12 | EX13 | EX14 | EX15 | EX16 | EX17 | EX18 | EX19 | EX20 |
|---|---|---|---|---|---|---|---|---|---|---|---|
| Component (A) | Type | A-1 | A-1 | A-1 | A-1 | A-1 | A-1 | A-1 | A-1 | A-1 | A-1 |
| | Content [part by mass] | 5.6 | 5.6 | 5.6 | 5.6 | 5.6 | 5.6 | 5.6 | 5.6 | 5.6 | 5.6 |
| Component (B) | Type | B-1 | B-1 | B-1 | B-1 | B-1 | B-1 | B-1 | B-1 | B-1 | B-1 |
| | Content [part by mass] | 1.4 | 1.4 | 1.4 | 1.4 | 1.4 | 1.4 | 1.4 | 1.4 | 1.4 | 1.4 |
| Component (C) | Type | C-12 | C-13 | C-14 | C-15 | C-16 | C-17 | C-18 | C-19 | C-20 | C-21 |
| | Particle diameter [μm] | 6.5 | 6.5 | 6.5 | 6.5 | 6.5 | 6.5 | 6.5 | 6.5 | 6.5 | 6.5 |
| | Surface treatment agent (S) | SL-3 | SL-4 | SL-5 | SZ-1 | SZ-2 | SZ-3 | SZ-4 | SZ-5 | SZ-6 | SZ-7 |
| | Treated amount [php] | 20 | 20 | 20 | 20 | 20 | 20 | 20 | 20 | 20 | 20 |
| | Content [part by mass] | 93 | 93 | 93 | 93 | 93 | 93 | 93 | 93 | 93 | 93 |
| Decrease in acoustic velocity | | B | B | B | B | B | A | B | B | A | A |
| Variations in AI | | B | B | B | A | A | A | A | A | A | A |

TABLE 4

Table 2-3

| | | EX21 | EX22 | EX23 | EX24 | EX25 | EX26 | EX27 | EX28 | EX29 | EX30 | EX31 |
|---|---|---|---|---|---|---|---|---|---|---|---|---|
| Component (A) | Type | A-1 | A-1 | A-1 | A-1 | A-1 | A-1 | A-1 | A-1 | A-1 | A-1 | A-1 |
| | Content [part by mass] | 5.6 | 5.6 | 5.6 | 5.6 | 5.6 | 5.6 | 6.4 | 6.4 | 4 | 6 | 5 |
| Component (B) | Type | B-1 | B-1 | B-1 | B-1 | B-1 | B-1 | B-1 | B-1 | B-1 | B-1 | B-1 |
| | Content [part by mass] | 1.4 | 1.4 | 1.4 | 1.4 | 1.4 | 1.4 | 1.6 | 1.6 | 1 | 1 | 2 |
| Component (C) | Type | C-22 | C-23 | C-24 | C-25 | C-26 | C-27 | C-8 | C-8 | C-8 | C-8 | C-8 |
| | Particle diameter [μm] | 3 | 9 | 15 | 6.5 | 6.5 | 6.5 | 6.5 | 6.5 | 6.5 | 6.5 | 6.5 |
| | Surface treatment agent (S) | ST-2 | ST-2 | ST-2 | ST-2 | ST-2 | ST-2 | ST-2 | ST-2 | ST-2 | ST-2 | ST-2 |
| | Treated amount [php] | 20 | 20 | 20 | 10 | 50 | 70 | 20 | 20 | 20 | 20 | 20 |
| | Content [part by mass] | 93 | 93 | 93 | 93 | 93 | 93 | 85 | 92 | 95 | 93 | 93 |
| Decrease in acoustic velocity | | A | A | A | A | A | B | C | A | A | A | B |
| Variations in AI | | A | A | B | A | A | A | A | A | B | A | A |

Table 2-4

| | | EX32 | EX33 | EX34 | EX35 | EX36 | EX37 | EX38 | EX39 | EX40 | EX41 | EX42 |
|---|---|---|---|---|---|---|---|---|---|---|---|---|
| Component (A) | Type | A-1 | A-1 | A-1 | A-1 | A-1 | A-1 | A-1 | A-1 | A-1 | A-2 | A-3 |
| | Content [part by mass] | 5.6 | 6.86 | 6.86 | 6.86 | 5.88 | 6.02 | 4.9 | 6.86 | 5.6 | 5.6 | 5.6 |
| Component (B) | Type | B-1 | B-2 | B-3 | B-4 | B-5 | B-6 | B-7 | B-8 | B-9 | B-1 | B-1 |
| | Content [part by mass] | 1.4 | 0.14 | 0.14 | 0.14 | 1.22 | 0.98 | 2.1 | 0.14 | 1.4 | 1.4 | 1.4 |
| Component (C) | Type | C-8 | C-8 | C-8 | C-8 | C-8 | C-8 | C-8 | C-8 | C-8 | C-8 | C-8 |
| | Particle diameter [μm] | 6.5 | 6.5 | 6.5 | 6.5 | 6.5 | 6.5 | 6.5 | 6.5 | 6.5 | 6.5 | 6.5 |
| | Surface treatment agent (S) | ST-2 | ST-2 | ST-2 | ST-2 | ST-2 | ST-2 | ST-2 | ST-2 | ST-2 | ST-2 | ST-2 |
| | Treated amount [php] | 20 | 20 | 20 | 20 | 20 | 20 | 20 | 20 | 20 | 20 | 20 |
| | Content [part by mass] | 93 | 93 | 93 | 93 | 93 | 93 | 93 | 93 | 93 | 93 | 93 |

TABLE 4-continued

| | | | | | | | | | | | |
|---|---|---|---|---|---|---|---|---|---|---|---|
| Decrease in acoustic velocity | A | B | B | B | A | A | A | B | B | A | A |
| Variations in AI | A | A | A | A | A | A | A | A | A | A | A |

TABLE 5

Table 2-5

| | | CEX1 | CEX2 | CEX3 | CEX4 | CEX5 |
|---|---|---|---|---|---|---|
| Component (A) | Type | A-1 | A-1 | A-1 | A-1 | A-1 |
| | Content [part by mass] | 5.6 | 49.4 | 49.4 | 49.4 | 49.4 |
| Component (B) | Type | B-1 | B-1 | B-1 | B-1 | B-1 |
| | Content [part by mass] | 1.4 | 0.6 | 0.6 | 0.6 | 0.6 |
| Component (C) | Type | W-2 | C-28 | C-29 | C-30 | C-2 |
| | Particle diameter [μm] | 6.5 | 6.5 | 6.5 | 6.5 | 6.5 |
| | Surface treatment agent (S) | — | SC-1 | SC-2 | SC-3 | SA-2 |
| | Treated amount [php] | 0 | 20 | 20 | 20 | 20 |
| | Content [part by mass] | 93 | 93 | 93 | 93 | 93 |
| Decrease in acoustic velocity | | F | E | E | E | E |
| Variations in AI | | E | D | D | D | D |

TABLE 6

Table 2-6

| | | EX43 | EX44 | EX45 | EX46 | EX47 | EX48 | EX49 | EX50 | EX51 |
|---|---|---|---|---|---|---|---|---|---|---|
| Component (A) | Type | A-1 | A-1 | A-1 | A-1 | A-1 | A-1 | A-1 | A-1 | A-1 |
| | Content [part by mass] | 5.6 | 5.6 | 5.6 | 5.6 | 5.6 | 5.6 | 5.6 | 5.6 | 5.6 |
| Component (B) | Type | B-1 | B-1 | B-1 | B-1 | B-1 | B-1 | B-1 | B-1 | B-1 |
| | Content [part by mass] | 1.4 | 1.4 | 1.4 | 1.4 | 1.4 | 1.4 | 1.4 | 1.4 | 1.4 |
| Component (C) | Type | C-31 | C-32 | C-33 | C-34 | C-35 | C-36 | C-37 | C-38 | C-39 |
| | Particle diameter [μm] | 6.5 | 6.5 | 6.5 | 6.5 | 6.5 | 6.5 | 6.5 | 6.5 | 6.5 |
| | Modification step | Done | Done | Done | Done | Done | Done | Done | Done | Done |
| | Surface treatment agent (S) | SA-1 | SM-1 | SM-2 | SI-1 | SI-2 | ST-1 | ST-2 | ST-3 | SL-1 |
| | Treated amount [php] | 20 | 20 | 20 | 20 | 20 | 20 | 20 | 20 | 20 |
| | Content [part by mass] | 93 | 93 | 93 | 93 | 93 | 93 | 93 | 93 | 93 |
| Decrease in acoustic velocity | | B | C | C | C | C | S | S | S | B |
| Variations in AI | | B | B | B | B | B | A | A | A | B |

Table 2-7

| | | EX52 | EX53 | EX54 | EX55 | EX56 | EX57 | EX58 | EX59 | EX60 |
|---|---|---|---|---|---|---|---|---|---|---|
| Component (A) | Type | A-1 | A-1 | A-1 | A-1 | A-1 | A-1 | A-1 | A-1 | A-1 |
| | Content [part by mass] | 5.6 | 5.6 | 5.6 | 5.6 | 5.6 | 5.6 | 5.6 | 5.6 | 5.6 |
| Component (B) | Type | B-1 | B-1 | B-1 | B-1 | B-1 | B-1 | B-1 | B-1 | B-1 |
| | Content [part by mass] | 1.4 | 1.4 | 1.4 | 1.4 | 1.4 | 1.4 | 1.4 | 1.4 | 1.4 |
| Component (C) | Type | C-40 | C-41 | C-42 | C-43 | C-44 | C-45 | C-46 | C-47 | C-48 |
| | Particle diameter [μm] | 6.5 | 6.5 | 6.5 | 6.5 | 6.5 | 6.5 | 6.5 | 6.5 | 6.5 |
| | Modification step | Done | Done | Done | Done | Done | Done | Done | Done | Done |

TABLE 6-continued

| | | | | | | | | | |
|---|---|---|---|---|---|---|---|---|---|
| Surface treatment agent (S) | SL-2 | SZ-3 | SZ-4 | SA-1 | SM-1 | ST-2 | ST-3 | SL-2 | SZ-3 |
| Treated amount [php] | 20 | 20 | 20 | 20 | 20 | 20 | 20 | 20 | 20 |
| Content [part by mass] | 93 | 93 | 93 | 93 | 93 | 93 | 93 | 93 | 93 |
| Decrease in acoustic velocity | A | S | A | C | C | S | S | A | S |
| Variations in AI | B | A | A | B | B | A | A | B | A |

<Notes of Table>

"EX": Example

"CEX": Comparative Example

Particle diameter: average primary particle diameter

"php": 100× parts by mass of surface treatment agent/100 parts by mass of tungsten carbide particles In Comparative Example 1, W-2 (untreated tungsten carbide particles) is described in the row of the component (C) for comparison.

[Epoxy Resin]

(A-1): Bisphenol A diglycidyl ether ("jER825" (trade name) manufactured by Mitsubishi Chemical Corporation, epoxy equivalent: 170)

(A-2): Bisphenol F diglycidyl ether ("EPICLON 830" (trade name) manufactured by DIC Corporation, epoxy equivalent: 170)

(A-3): Epoxy novolac resin (manufactured by Sigma-Aldrich Co. LLC, product number 406775, epoxy equivalent: 170)

(B-1):
Isophorone (B-2):
Triethylenetetramine (B-3):
2,4,6-Tris(dimethylaminomethyl)phenol (manufactured by Nacalai Tesque Inc., trade name: "LUVEAK DMP-30")

(B-4):
Polyamide amine (manufactured by DIC Corporation, trade name: "LUCKAMIDE EA-330")

(B-5):
Menthanediamine (B-6):
m-Phenylenediamine (B-7):
Polyetheramine T-403 (trade name, manufactured by BASF SE)

(B-8):
2-Ethyl-4-methylimidazole (B-9):
Hexahydrophthalic anhydride (manufactured by New Japan Chemical Co., Ltd., trade name: "RIKACID HH")

As shown in Table 2, the acoustic matching sheet of Comparative Example 1, in which untreated tungsten carbide particles were used, had a significant decrease in acoustic velocity and a large variation in AI.

In the acoustic matching sheet of Comparative Example 2, in which tungsten carbide particles surface-treated with methyltrichlorosilane were used, since the compatibility of these particles in a case of being mixed with the epoxy resin was poor, and the acoustic matching sheet was a sheet in which the particles were unevenly dispersed due to heat generation, the acoustic velocity was decreased significantly and the variations in AI was large.

In the acoustic matching sheet of Comparative Example 3, in which tungsten carbide particles surface-treated with vinyltrichlorosilane were used, and in the acoustic matching sheet of Comparative Example 4, in which tungsten carbide particles surface-treated with 3-methacryloxypropyltrimethoxysilane were used, the acoustic velocity was decreased significantly and the variations in AI was large for the same reason as in Comparative Example 2.

On the other hand, it can be seen that all of the acoustic matching sheets of Examples 1 to 60, in which the surface-treated tungsten carbide particles specified in the present invention were used, could effectively suppress the decrease in acoustic velocity and could also suppress the variations in acoustic characteristics.

All of the acoustic matching sheets of Examples 1 to 60 had sufficient AI to be used as an acoustic matching layer on a piezoelectric element side.

EXPLANATION OF REFERENCES

1: acoustic lens
2: acoustic matching layer
3: piezoelectric element layer
4: backing material
7: housing
9: cord
10: ultrasound probe

What is claimed is:

1. A material for an acoustic matching layer, comprising the following components (A), (B), and (C):
(A) an epoxy resin;
(B) a curing agent; and
(C) surface-treated tungsten carbide particles subjected to a surface treatment with a surface treatment agent including at least one of an aminosilane compound, a mercaptosilane compound, an isocyanatosilane compound, a thiocyanatosilane compound, an aluminum alkoxide compound including at least one of an acetonato structure or an acetato structure, a zirconium alkoxide compound, or a titanium alkoxide compound.

2. The material for an acoustic matching layer according to claim 1,
wherein the component (B) includes at least one of a primary amine or a secondary amine.

3. The material for an acoustic matching layer according to claim 1,
wherein the surface treatment agent includes at least one of an aminosilane compound, an aluminum alkoxide compound, a zirconium alkoxide compound, or a titanium alkoxide compound.

4. The material for an acoustic matching layer according to claim 1,
wherein the surface treatment agent includes at least one of an aluminum alkoxide compound, a zirconium alkoxide compound, or a titanium alkoxide compound.

5. The material for an acoustic matching layer according to claim 1, wherein the surface treatment agent includes at least one of a zirconium alkoxide compound or a titanium alkoxide compound.

6. The material for an acoustic matching layer according to claim 1, wherein the aluminum alkoxide compound includes at least one compound represented by General Formula (1), $R^{1a}_{m1}$-Al—$(OR^{2a})_{3-m1}$ General Formula (1):

where $R^{1a}$ represents a hydrogen atom, an alkyl group, a cycloalkyl group, an acyl group, an aryl group, or an unsaturated aliphatic group, $R^{2a}$ represents a hydrogen atom, an alkyl group, a cycloalkyl group, an acyl group, an alkenyl group, an aryl group, a phosphonate group, or —$SO_2R^{S1}$, $R^{S1}$ represents a substituent, and m1 is an integer of 0 to 2.

7. The material for an acoustic matching layer according to claim 1, wherein the zirconium alkoxide compound includes at least one of an acetonato structure or an acetato structure.

8. The material for an acoustic matching layer according to claim 1, wherein the zirconium alkoxide compound includes at least one compound represented by General Formula (2), $R^{1b}_{m2}$-Zr—$(OR^{2b})_{4-m2}$ General Formula (2):

where $R^{1b}$ represents a hydrogen atom, an alkyl group, a cycloalkyl group, an acyl group, an aryl group, or an unsaturated aliphatic group, $R^{2b}$ represents a hydrogen atom, an alkyl group, a cycloalkyl group, an acyl group, an alkenyl group, an aryl group, a phosphonate group, or —$SO_2R^{S2}$, $R^{S2}$ represents a substituent, and m2 is an integer of 0 to 3.

9. The material for an acoustic matching layer according to claim 1, wherein the titanium alkoxide compound includes at least one atom of N, P, or S.

10. The material for an acoustic matching layer according to claim 1, wherein the titanium alkoxide compound includes at least one compound represented by General Formula (3), $R^{1c}_{m3}$-Ti—$(OR^{2c})_{4-m3}$ General Formula (3):

where $R^{1c}$ represents a hydrogen atom, an alkyl group, a cycloalkyl group, an acyl group, an aryl group, or an unsaturated aliphatic group, $R^{2c}$ represents a hydrogen atom, an alkyl group, a cycloalkyl group, an acyl group, an alkenyl group, an aryl group, a phosphonate group, or —$SO_2R^{S3}$, $R^{S3}$ represents a substituent, and m3 is an integer of 0 to 3.

11. The material for an acoustic matching layer according to claim 1, wherein a content of the surface treatment agent in the component (C) is 1 to 50 parts by mass with respect to 100 parts by mass of the surface-treated tungsten carbide particles.

12. The material for an acoustic matching layer according to claim 1, wherein an average primary particle diameter of the surface-treated tungsten carbide particles constituting the component (C) is 1 to 10 μm.

13. An acoustic matching sheet obtained by curing the material for an acoustic matching layer according to claim 1.

14. An acoustic wave probe comprising:

the acoustic matching sheet according to claim 13.

15. An acoustic wave measurement apparatus comprising:

the acoustic wave probe according to claim 14.

16. An ultrasound probe comprising:

the acoustic matching sheet according to claim 13.

17. An ultrasound diagnostic apparatus comprising:

the ultrasound probe according to claim 16.

18. A method for manufacturing an acoustic wave probe, comprising:

forming an acoustic matching layer using the material for an acoustic matching layer according to claim 1.

19. A material for an acoustic matching layer, comprising the following components (A), (B), and (C):

(A) an epoxy resin;

(B) a curing agent; and (C) surface-treated tungsten carbide particles subjected to a surface treatment with a surface treatment agent including a zirconium alkoxide compound, wherein the zirconium alkoxide compound includes at least one compound represented by General Formula (2), $R^{1b}_{m2}$-Zr—$(OR^{2b})_{4-m2}$ General Formula (2):

where $R^{1b}$ represents a hydrogen atom, an alkyl group, a cycloalkyl group, an acyl group, an aryl group, or an unsaturated aliphatic group, $R^{2b}$ represents a hydrogen atom, an alkyl group, a cycloalkyl group, an acyl group, an alkenyl group, an aryl group, a phosphonate group, or —$SO_2R^{S2}$, $R^{S2}$ represents a substituent, and m2 is an integer of 0 to 3.

20. A material for an acoustic matching layer, comprising the following components (A), (B), and (C):

(A) an epoxy resin;

(B) a curing agent; and (C) surface-treated tungsten carbide particles subjected to a surface treatment with a surface treatment agent including a titanium alkoxide compound, wherein the titanium alkoxide compound includes at least one compound represented by General Formula (3), $R^{1c}_{m3}$-Ti—$(OR^{2c})_{4-m3}$ General Formula (3):

where $R^{1c}$ represents a hydrogen atom, an alkyl group, a cycloalkyl group, an acyl group, an aryl group, or an unsaturated aliphatic group, $R^{2c}$ represents a hydrogen atom, an alkyl group, a cycloalkyl group, an acyl group, an alkenyl group, an aryl group, a phosphonate group, or —$SO_2R^{S3}$, $R^{S3}$ represents a substituent, and m3 is an integer of 0 to 3.

* * * * *